United States Patent [19]
Cundari et al.

[11] Patent Number: 5,989,199
[45] Date of Patent: Nov. 23, 1999

[54] TISSUE EXAMINATION

[75] Inventors: Michael A. Cundari, Hingham; Alan I. West, Hopkinton; Richard H. Theriault, Lincoln; Brian D. Noble, Weymouth; David R. Widder, Newton, all of Mass.

[73] Assignee: Assurance Medical, Inc., Hopkinton, Mass.

[21] Appl. No.: 08/757,466

[22] Filed: Nov. 27, 1996

[51] Int. Cl.$^6$ ................................................. A61B 5/103
[52] U.S. Cl. ............................................ 600/587; 600/595
[58] Field of Search .................................. 600/587, 594, 600/595

[56] References Cited

U.S. PATENT DOCUMENTS

| Re. 30,446 | 12/1980 | Meyers et al. | 128/736 |
|---|---|---|---|
| Re. 32,000 | 10/1985 | Sagi | 128/736 |
| 3,154,789 | 11/1964 | Lewis, Jr. | 2/104 |

(List continued on next page.)

FOREIGN PATENT DOCUMENTS

| PCT/US96/17173 | 10/1996 | European Pat. Off. . |
|---|---|---|
| 2 086 575 | 5/1982 | United Kingdom . |

OTHER PUBLICATIONS

E.J. Chen et al., "Ultrasound Tissue Displacement Imaging with Application to Breast Cancer", 1995, Ultrasound in Med. & Biol., vol. 21, No. 9, pp. 1153–1156, Michigan, U.S.A.

R.S. Fearing et al., "A Tactile Sensing Finger Tip for a Dextrous Hand", Oct. 1986, 5th SPIE Intelligent Robotics and Computer Vision, pp. 1–10, Cambridge, Massachusetts.

Brian S. Garra, et al. "Elastography of Breast Lesions: Initial Clinical Results" 1997, Radiology, vol. 202, pp. 69–86.

F. Kallel et al., "Fundamental Limitations on the Contrast–Transfer Efficiency in Elastography: an Analytic Study", 1996, Ultrasound in Med. & Biol., vol. 22, No. 4, pp. 463–470.

Dr. Ricki Lewis, "New Imaging Technology May Detect Early Cancer", Biophotonics in Action, Oct. 1996, Photonics Spectra, pp. 52–53.

G. Piperno et al., "Breast Cancer Screening by Impedance Measurements", 1990, Frontiers Med. Biol. Engng. vol. 2, No. 2, pp. 111–117.

G.I. Pressman et al., "A Transducer for the Continuous External Measurement of Arterial Blood Pressure", 1960s, IEEE Transactions on Bio–Medical Electronics.

Martin Feder et al., "Transducer Characteristics for Ultrasonic Stereoholography", Dec. 1976, Bull. N.Y. Acad. Med., vol. 52, No. 10, pp. 1207–1223.

B.D. Sollish et al., "Microprocessor–Assisted Screening Techniques", 1981, Israel J. Med. Sci., pp. 859–864, Israel.

R.G. Stevens et al., "The use of Difference of Gaussian Image Filtering to Assess Objectively the Correlations Between Breast Vascularity and Breast Cancer", 1988, Phys. Med. Biol., vol. 33, No. 12, pp. 1417–1431, U.K.

John D. Laird et al., Tissue Examination; Filed Nov. 9, 1995, USSN 08/556,161; Batch No. E92.

Allowed claims in John D. Laird et al., Tissue Examination; Filed Nov. 9, 1995, USSN 08/556,161; Batch No. E92.

*Primary Examiner*—Cary O'Connor
*Assistant Examiner*—Pamela L. Wingood
*Attorney, Agent, or Firm*—Fish & Richardson P.C.

[57] ABSTRACT

A tissue examination device includes a plurality of sensors, each of which produces a signal in response to pressure imposed on the sensor in accordance with the properties of different types of underlying tissue structures as the sensor is pressed against the tissue. A plurality of processing tests are performed on the signals, and the different types of the underlying tissue structures are discriminated from each other based on the results of the tests.

93 Claims, 14 Drawing Sheets

U.S. PATENT DOCUMENTS

| | | | |
|---|---|---|---|
| 3,308,476 | 3/1967 | Kleesattel . | |
| 3,323,352 | 6/1967 | Branson . | |
| 3,744,490 | 7/1973 | Fernandez | 128/2.05 |
| 3,847,139 | 11/1974 | Flam | 128/2 H |
| 3,854,471 | 12/1974 | Wild | 128/2 V |
| 3,880,145 | 4/1975 | Blick | 128/2.05 |
| 3,970,862 | 7/1976 | Edelman et al. | 307/88 ET |
| 3,972,227 | 8/1976 | Tomilov | 73/67.7 |
| 3,996,922 | 12/1976 | Basham | 128/2 R |
| 4,001,951 | 1/1977 | Fasse | 35/17 |
| 4,023,562 | 5/1977 | Hynecek et al. | 128/2.05 E |
| 4,025,165 | 5/1977 | Sollish et al. | 350/161 S |
| 4,132,224 | 1/1979 | Randolph | 128/2 S |
| 4,134,218 | 1/1979 | Adams et al. | 35/17 |
| 4,135,497 | 1/1979 | Meyers et al. | 128/2 H |
| 4,144,877 | 3/1979 | Frei et al. | 128/2 S |
| 4,159,640 | 7/1979 | Leveque et al. | 73/81 |
| 4,190,058 | 2/1980 | Sagi | 128/736 |
| 4,212,306 | 7/1980 | Mahmud | 128/665 |
| 4,219,708 | 8/1980 | Rubey | 200/61.47 |
| 4,250,894 | 2/1981 | Frei et al. | 128/774 |
| 4,286,602 | 9/1981 | Guy | 128/660 |
| 4,291,708 | 9/1981 | Frei et al. | 128/734 |
| 4,458,694 | 7/1984 | Sollish et al. | 128/734 |
| 4,503,865 | 3/1985 | Shishido | 128/774 |
| 4,524,778 | 6/1985 | Brown, Jr. et al. | 128/736 |
| 4,555,953 | 12/1985 | Dario et al. | 73/862.04 |
| 4,570,638 | 2/1986 | Stoddart et al. | 128/665 |
| 4,600,011 | 7/1986 | Watmough | 128/664 |
| 4,641,659 | 2/1987 | Sepponen | 128/653 |
| 4,641,661 | 2/1987 | Kalarickal | 128/744 |
| 4,651,749 | 3/1987 | Sagi | 128/736 |
| 4,657,021 | 4/1987 | Perry et al. | 128/630 |
| 4,729,378 | 3/1988 | Trittenbass | 128/645 |
| 4,737,109 | 4/1988 | Abramson | 434/267 |
| 4,768,516 | 9/1988 | Stoddart et al. | 128/665 |
| 4,774,961 | 10/1988 | Carr | 128/736 |
| 4,790,329 | 12/1988 | Simon | 128/749 |
| 4,793,354 | 12/1988 | Wright et al. | 128/630 |
| 4,807,637 | 2/1989 | Bjorkhom | 128/664 |
| 4,810,875 | 3/1989 | Wyatt | 250/227 |
| 4,817,623 | 4/1989 | Stoddart et al. | 128/665 |
| 4,873,982 | 10/1989 | Morrison | 128/630 |
| 4,886,070 | 12/1989 | Demarest | 128/675 |
| 4,944,298 | 7/1990 | Sholder | 607/14 |
| 5,010,772 | 4/1991 | Bourland et al. | 73/862.04 |
| 5,012,817 | 5/1991 | Zeilinski et al. | 128/744 |
| 5,031,634 | 7/1991 | Simon | 128/754 |
| 5,079,698 | 1/1992 | Grenier et al. | 364/413.13 |
| 5,099,848 | 3/1992 | Parker et al. | 128/661.07 |
| 5,140,989 | 8/1992 | Lewis et al. | 128/665 |
| 5,143,079 | 9/1992 | Frei et al. | 128/734 |
| 5,212,637 | 5/1993 | Saxena | 364/413.26 |
| 5,221,269 | 6/1993 | Miller et al. | 604/281 |
| 5,265,612 | 11/1993 | Sarvazyan et al. | 128/660.01 |
| 5,301,681 | 4/1994 | DeBan et al. | 128/736 |
| 5,301,682 | 4/1994 | Debbas | 128/737 |
| 5,333,612 | 8/1994 | Wild | 128/660.9 |
| 5,511,561 | 4/1996 | Wanderman et al. | 128/779 |
| 5,524,636 | 6/1996 | Sarvazyan et al. . | |
| 5,678,565 | 10/1997 | Sarvazyan . | |
| 5,785,663 | 7/1998 | Sarvazyan | 600/587 |
| 5,795,308 | 8/1998 | Russin | 600/567 |
| 5,807,276 | 9/1998 | Russin | 600/567 |
| 5,833,634 | 11/1998 | Laird et al. | 600/587 |

TISSUE EXAMINATION

BACKGROUND

This invention relates to tissue examination, and in particular to detecting foreign structures in, e.g., breast tissue.

One traditional way of examining breast tissue to detect foreign structures such as lumps is to palpate the breast manually. For example, the patient firmly presses on the breast with three fingers while moving the fingers in a circular palpating motion. Typically, such manual breast self-examinations can detect lumps as small as a few centimeters in diameter.

Instruments for electronically examining the breast are available. One such instrument includes an array of pressure sensors which is pressed against the breast. Each pressure sensor in the array generates an electrical signal proportional to the local pressure imposed on the sensor when the array is pressed against the breast. When adjacent sensors are positioned across the boundary of a lump within the breast tissue, the sensor that lies over the lump generates an electrical signal indicating the detection of greater local pressure than the adjacent transducer element, which is located over soft tissue alone. The instrument determines whether a lump is present by analyzing the differences between the electrical signals generated by the sensors.

SUMMARY

This invention concerns examining tissue with a plurality of sensors, each of which produces a signal in response to pressure imposed on the sensor in accordance with the properties of different types of underlying tissue structures as the sensor is pressed against the tissue. In one general aspect, the invention features performing a plurality of processing tests on the signals, and discriminating between the different types of the underlying tissue structures based on the results of the tests.

The processing tests serve two purposes. The first is to determine the pressure signature of the underlying tissue structure—that is, the manner in which the tissue structure responds to applied pressure. The tests also compare the pressure signature to pressure signatures which have been empirically determined to correspond to structures normally found in the breast (such as the nipple, the inframammary ligament, or ribs), and potentially foreign structures (such as cysts, benign masses, or carcinomas), thereby providing a sensitive, yet accurate, way of discriminating between the normal and potentially foreign structures.

Preferred embodiments may include one or more of the following features.

Normal tissue structures are discriminated from potentially foreign tissue structures based on the results of the tests, and a user is notified as to whether an underlying tissue structure is a potentially foreign tissue structure. For example, different indicators are actuated to indicate whether the underlying tissue structure is a potentially foreign tissue structure or is a normal tissue structure. Signals corresponding to the amplitudes of the signals produced by the sensors may be displayed to allow the user to visualize the pressure signature.

The sensors are arranged in an array. The array may include multiple rows of sensors or a single row of sensors. The individual sensors are, e.g., resistive elements, piezoelectric elements, or capacitive sensors.

The processing tests preferably are performed only if the user is applying the correct amount of pressure to the array against the body. The signals produced by the sensors are analyzed to determine the amount of pressure applied to the sensors by the user. If the amount of pressure is outside of a selected range of pressures, the processing tests are terminated. Otherwise, the user is notified that the correct amount of pressure is being applied.

The processing tests include a first test that determines whether the amplitudes of the signals produced by the sensors are sufficient to indicate that a suspicious underlying structure may be present. In the first test, the signal amplitudes are compared to a threshold, and signals that exceed the threshold are evaluated differently from signals that do not exceed the threshold. Preferably, the threshold is dynamic, e.g., is generated based on the signal amplitudes. The first test also determines whether an average of the signal amplitudes that exceed the threshold is within a predetermined range of amplitudes, and whether an average of the signal amplitudes that do not exceed the threshold exceeds a selected minimum amplitude. The first test passes if these averages are within the limits and exceed the selected minimum amplitude, respectively; otherwise the first test fails.

Edge filtering is applied to the signals that exceed the threshold to determine whether signals produced by sensors on the periphery of the array are valid or are instead due to "edge effects" caused by improper operation by the user. This is done by comparing a first number of adjacent sensors arranged on the periphery that produce signals which exceed the threshold to a second number of adjacent sensors arranged in an interior of the array that produce signals which exceed the threshold. The signals produced by sensors arranged on the periphery are determined to be valid if the second number exceeds the first number by a selected amount. If the signals produced by the sensors on the periphery of the array are determined to be invalid, their amplitudes are reduced to below the threshold applied in the first test.

A second processing test determines whether any suspicious underlying regions are sufficiently large and sufficiently predominate nearby suspicious regions to warrant further testing. In the second test, the relative locations in the array of sensors that produce signals which exceed the threshold are identified. Then, a determination is made as to how many of these sensors are located adjacent to another sensor in the array that produces a signal which exceeds the threshold. The second test fails unless the number of such adjacent sensors exceeds a selected minimum number (that is, unless the suspicious region has a selected minimum size). The second test checks for the predominance of the suspicious region by determining whether the number of such adjacent sensors exceeds by a selected amount an aggregate of the number of such sensors and a number of nonadjacent sensors in the array that produce signals that exceed the threshold. If so, the second test passes; otherwise, the second test fails.

A third processing test determines whether the suspicious region is flat (as are normal structures such as the nipple and the inframammary ligament) or peaked (as are foreign structures such as cysts and other lumps). The third test determines the maximum difference between the amplitudes of the signals that exceed the threshold, e.g., by determining a ratio between the signal having a highest amplitude and the signal having a lowest amplitude. The third test passes if this ratio exceeds a second threshold, and fails otherwise.

During use, a plurality of sets of the signals are acquired from the sensors at successively different times as the array is moved over the tissue. The sets of signals represent the underlying tissue structures at these times. The sets of signals are stored, and the above processing tests are preformed on each set of signals.

Additional processing tests are performed on a selected number of the sets of signals that have passed the first, second, and third tests. Preferably, the additional processing tests are performed only if the selected number of the sets of signals are consecutively acquired without interruption by a set of the signals that do not pass either the first, second, or third test. This requirement helps reduce the possibility of false positive results.

The additional tests include a fourth test that examines pressure profiles of each suspicious region to determine whether the suspicious region has lump-like characteristics. A pair of pressure profiles are developed for each suspicious region by analyzing, for each of the sets of the signals, the amplitudes of the signals that exceed the threshold. Each pressure profile comprises signals produced by sensors in the array that are arranged along a selected dimension of a corresponding suspicious region. A first pressure profile is oriented along a dimension of maximum flatness of the region, and a second pressure profile is oriented along a dimension of minimum flatness of the region.

In the fourth test, an edge profile, a relative stiffness, and a relative curvature of each suspicious region are determined based on the first and second pressure profiles. The edge profile is determined based on an amount that the amplitude of the signals change from sensor to sensor along the second pressure profile. The relative stiffness is obtained based on a difference between the signal having a highest amplitude and the signal having a lowest amplitude in the first pressure profile. The relative curvature is determined based on the flatness of the first pressure profile.

The edge profile, the relative stiffness, and the relative curvature of each suspicious region are evaluated with respect to each other, and an outcome is developed based on the evaluation. The outcome indicates a degree of membership of each suspicious region in a class of foreign tissue structures. That is, the outcome is not simply a binary result based on whether a given test "passes" or "fails"; rather, the degrees to which the standards applied by the tests are met by the suspicious region are evaluated and weighed (either equally, or not) to determine whether the characteristics of the region sufficiently resemble those of foreign tissue structures such as a lump. One example of a procedure for performing such an evaluation is a so-called "fuzzy logic" technique, which employs neural network concepts for developing parameters of imprecise measurements.

The additional tests include a fifth test in which the sets of the signals are evaluated to determine the manner in which each of the suspicious regions moves with respect to the array as the array is moved over the tissue. This provides an indication of whether the regions are mobile in the body in a manner consistent with the mobility of lumps or other foreign structures. Preferably, the fifth test is performed by determining the distance and trajectory of each region's movement with respect to the array. The distance and trajectory of the suspicious region are evaluated with respect to each other, and an outcome is developed based on the evaluation that indicates a degree of membership of each suspicious region in a class of foreign tissue structures. Different weights may be assigned to the distance and trajectory determinations, or not. The edge profile, the relative stiffness, and the relative curvature of each suspicious region is also taken into account in developing the outcome. Preferably, the "fuzzy logic" techniques discussed above are used.

The invention provides a highly sensitive, yet specific, technique for discriminating potentially foreign tissue structures from normal tissue. The invention is easy to use (e.g., using a hand-held device that embodies the techniques described above) and can be used in the privacy of the patient's home. If the device indicates the a potential foreign structure is present, the user may check with her physician for further testing.

Other advantages and features will become apparent from the following description and from the claims.

DRAWINGS

DESCRIPTION

Figure 1:
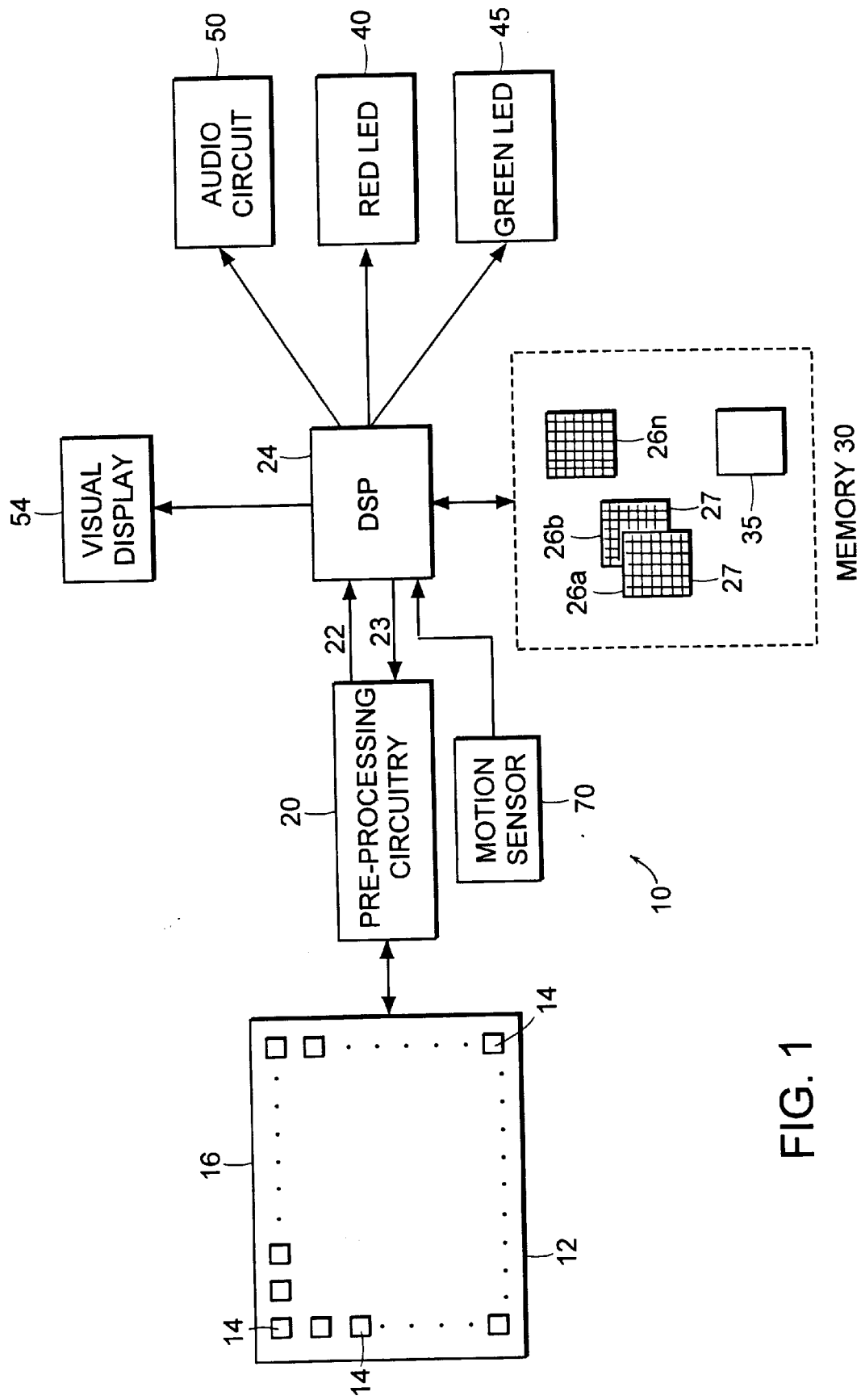
FIG. 1 is a block diagram of a tissue examination device.

Referring to FIG. 1, tissue examination device 10 includes an array 12 of pressure sensors 14 carried on a thin, flexible membrane 16. Array 12 is, for example, a contact sensor such as that described in U.S. Pat. No. 4,856,993, entitled "Pressure and Contact Sensor System for Measuring Dental Occlusion" (the '993 patent), incorporated herein by reference, the individual pressure sensors 14 of which are resistive elements. Pressure sensors 14 are arranged in an orthogonal grid of rows and columns in array 12. Pressure sensors 14 are relatively small and are closely spaced to provide high resolution capable of distinguishing between areas of underlying tissue separated by 1 mm or less. Array 12 is commercially available from Tekscan, Inc. (the assignee of the '993 patent).

Figure 2:
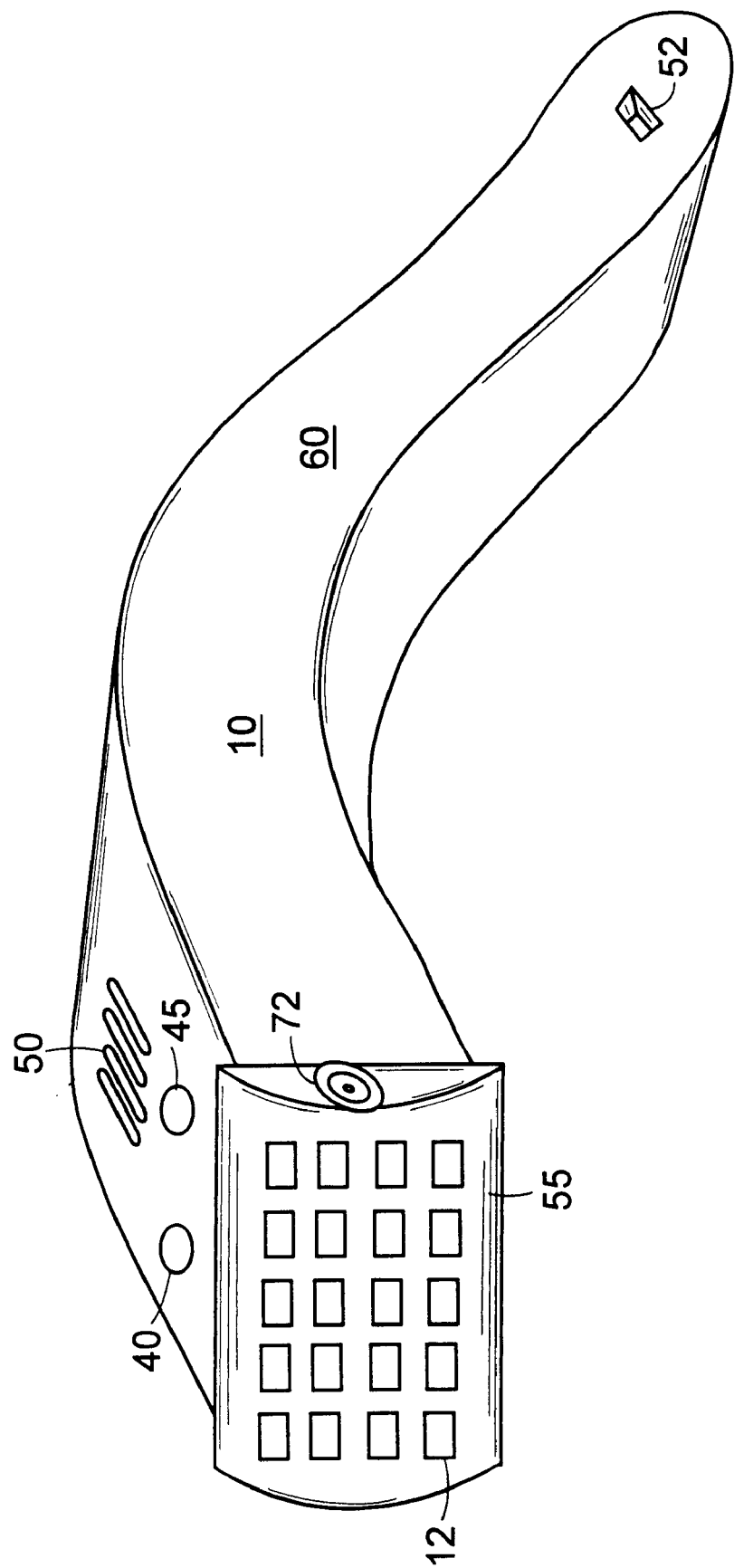
FIG. 2 shows one embodiment of the tissue examination device of FIG. 1.

Referring also to FIG. 2, array 12 is mounted on a sensor head 55 made from a rigid polymer such as polycarbonate. (In FIG. 2, array 12 is shown as including twenty sensors 14; it will be understood that the number of sensors 14 in array 12 is typically much larger.) Sensor head 55 is attached to a handle 60 which is grasped by a user to place array 12 against the tissue to be examined (such as the user's breast). The face of sensor head 55 on which array 12 is mounted is convex, with a radius of curvature of approximately 1.5 inches to enhance the mechanical coupling between sensors 14 and the underlying tissue. In use, head 55 is manually translated across the skin by the user applying pressure with her hand placed on handle 60. The translation technique is essentially a series of stationary palpations which allow the user to increase breast area coverage with less exam time.

The resistance of each pressure sensor 14 changes in accordance with the amount of pressure applied to sensor 14. The resistance change is inversely proportional to the pressure imposed on sensor 14. Thus, the resistance of each sensor 14 decreases as applied pressure increases.

Generally, the pressure imposed on the sensors 14 increases when the sensors 14 are pressed against localized areas of stiffer tissue on, within, or below the softer breast tissue. Examples of such stiffer tissue include normal breast tissue structures—such as the nipple, the inframammary ligament, and underlying ribs—and foreign bodies such as cysts and solid masses (whether or not pathogenic). Consequently, as array 12 is pressed and moved against the breast, the pressure imposed on sensors 14 and, thus the resistance of sensors 14, varies in accordance with the properties of the underlying tissue structures.

The individual resistances of pressure sensors 14 are read by preprocessing circuitry 20, the output 22 of which is applied to a digital signal processor (DSP) 24. Briefly, preprocessing circuitry 20 sequentially measures the resistance of pressure sensors 14 in response to row and column address signals 23 provided by DSP 24 to provide an indication of pressure applied to the location in array 12 that corresponds to that sensor 14. During each resistance measurement, preprocessing circuitry 20 applies a reference potential (not shown) to the addressed sensor 14, measures the voltage drop induced across that sensor 14, and generates an output 22 corresponding to the voltage drop. Thus, each pressure sensor 14 produces a signal (in this example, resistance-induced voltage) in response to the applied pressure. The operation of preprocessing circuitry is more fully described in the '993 patent.

The preprocessor output signals 22 are digitized (by A/D converters, not shown) and applied to DSP 24 (alternatively, an input stage of DSP 24 may perform the A/D conversion). The set of sequentially produced output signals 22 for all pressure sensors 14 in array 12 is termed a "frame." DSP 24 addresses preprocessing circuitry 20 at a rate sufficient to read 8 frames or more of output signals 22 per second. DSP 24 stores each frame of signals 22 in an area 26a–26n of memory 30. Each memory area 26a–26n contains storage locations 27 which respectively correspond to the locations of pressure sensors 14 in array 12. Thus, each memory area 26a–26n contains a "map" of the pressures detected by pressure sensors 14 in a frame. This map can be viewed as a "pressure signature" of the tissue structures beneath array 12. Accordingly, memory areas 26a–26n contain a time sequence of pressure signatures of the underlying tissue as array 12 is palpated across the breast.

We have found that different types of tissue structures have different pressure signatures which can be used to differentiate the tissue structure types from each other. The pressure signatures result from the way in which the tissue structures respond to being stressed by the pressures exerted when the user moves array 12 over the breast. The stiffness (elasticity) of a given tissue structure, its composition (e.g., percentage of fat, presence of ducts, and fibrous tissue), its density, and the degree to which the tissue structure is held in place by surrounding tissue are all factors that contribute to the pressure signature of the tissue structure. Another factor which affects the resulting pressure signature is whether anatomical structures (e.g. ribs) lie beneath the tissue structure. These factors, in combination, are sufficiently different for various types of tissue structures (e.g., normal breast structures such as ribs, nipples, ligaments, etc., and foreign structures such as cysts, solid masses, and other lumps with respect to normal tissue stiffness) that the pressure signatures of these structures are distinguishable from each other.

As described in detail below, DSP 24 performs various processing tests defined by an operating program 35 stored in memory 30 on the pressure signatures stored in memory areas 26a–26n. The tests enable DSP 24 to discriminate normal underlying tissue structures from potentially foreign structures. If DSP 24 determines a potentially foreign tissue structure is present, DSP 24 notifies the user by illuminating a red LED 40. A green LED 45 is illuminated when device 10 is powered on. Green LED 45 remains illuminated throughout the tissue examination procedure as a system self check. In addition, an audio circuit 50, such as a buzzer, a tone generator, or both may be actuated by DSP 24 in conjunction with LEDs 40, 45, as discussed below. Handle 60 also includes a communication port 52 for coupling the maps of signals 22 to a visual display 54, thereby allowing the user to observe the pressure signatures directly.

Device 10 also contains motion sensor 70 that detects the motion of head 55 across the tissue and sends this information to DSP 24 for use in determining the motion of sensor head 55. This allows DSP 24 to analyze movement of the underlying tissue structure when the sensor head 55 is translated over the tissue. Motion sensor 70 derives the motion information from the rotation of a roller 72 connected to head 55.

Figure 3:
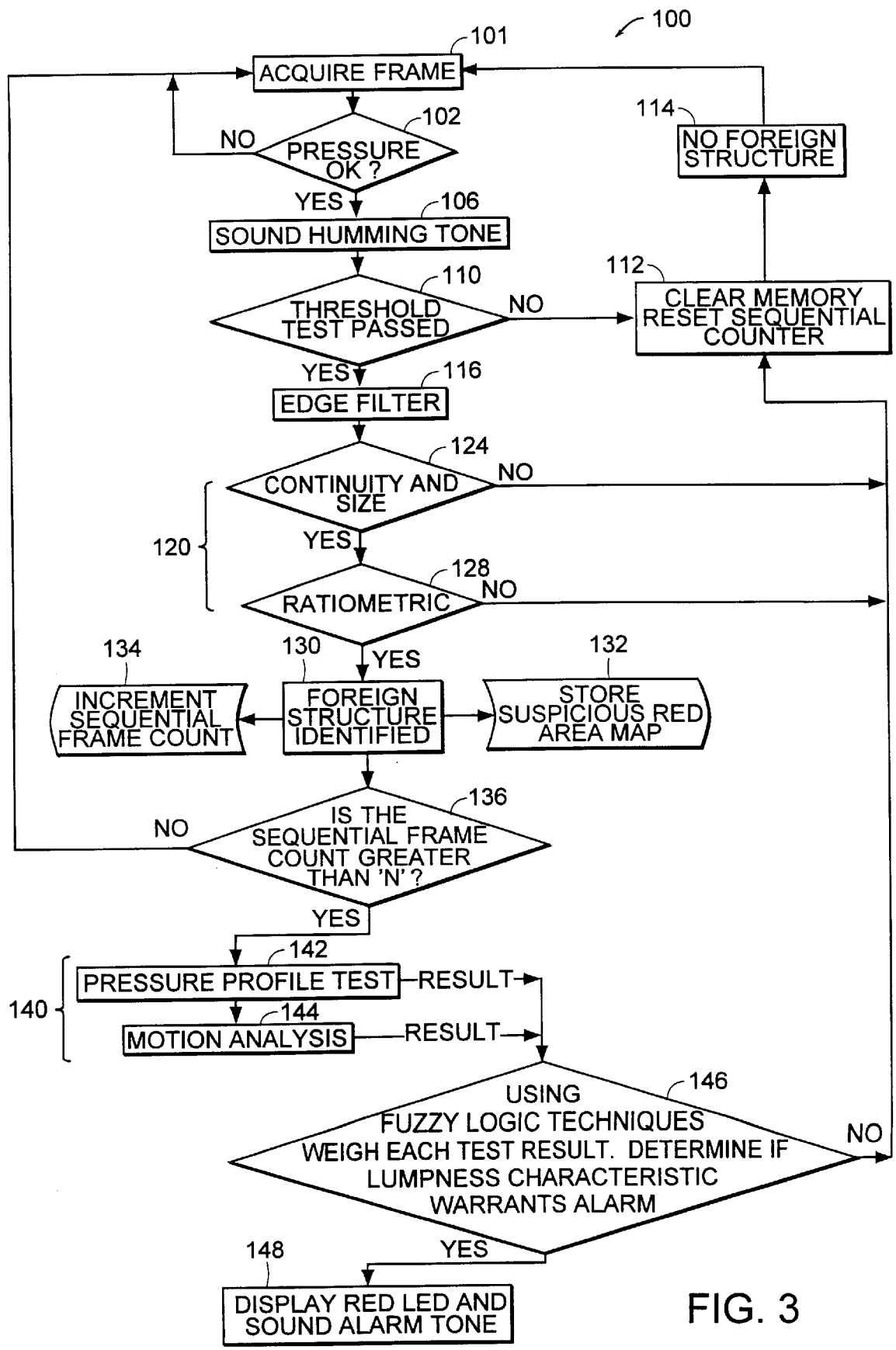
FIG. 3 is a flow chart showing the operation of the tissue examination device of FIG. 1.

FIG. 3 is a flow chart of a procedure 100 of processing tests performed by DSP 24 on each frame of signals 22 stored in memory areas 26a–26n. Test procedure 100 is discussed briefly below, and then in more detail after the pressure signatures of various tissue structures are described with reference to FIGS. 4A–8B. Preliminarily, note that the pressure signatures are a function of the amount of average pressure applied to sensors 14 when the user presses array 12 against the body. The pressure applied by the user should be within a selected range in order for the pressure signatures to accurately correspond to the various tissue structure types. The limits of the pressure range are a function of size and sensitivity of the array 12. For array 12 discussed above, the acceptable pressure range is 0.2 psi to 2 psi.

Because the proper amount of user-applied pressure is important, a preliminary test 102 is performed on the frame to determine whether the average amount of pressure applied to all sensors 14 is within the acceptable range. Preliminary test 102 also determines if a minimum number of sensors 14 are obtaining a reading across width of array 12 such that DSP 24 recognizes that entire array 12 is in contact with the skin. If the frame fails test 102 (e.g., if the average applied pressure is below or above the acceptable range), the frame is considered invalid and is not examined further in test procedure 100, and DSP 24 proceeds to the next frame stored in memory 30 (101). If the frame passes initial test 102, DSP 24 triggers audio circuit 50 to produce a low pitched humming tone (106). DSP 24 maintains this tone throughout test procedure 100 to give the user feedback that the applied pressure is correct.

When the user is applying the correct amount of pressure, DSP 24 performs a series of tests 110, 120, 140 on each frame to determine the pressure signature defined by signals 22 in the frame. Briefly, in test 110, DSP 24 analyzes the amplitude of each signal 22 to determine whether it is above or below a pressure threshold that is dynamically determined for that frame. Those signals 22 in the frame that exceed the pressure threshold are termed "suspicious signals" 22 or "red signals" 22. Signals in the frame that do not exceed the pressure threshold are called "blue signals."

As discussed below, DSP 24 then applies different thresholds to the red and blue signals 22 to analyze whether both types of signals are consistent with the presence of potentially foreign underlying tissue structures. If so, the frame passes threshold test 110, and after edge filter analysis 116 (discussed below) is performed, subsequent tests 120, 140 are performed on the red signals 22 in the frame (the blue signals 22, which are too low in amplitude to correspond to a potentially foreign structure, are not tested further). If threshold test 110 fails, DSP 24 clears that frame from memory 30 and resets a sequential counter (112) (discussed below), and proceeds to the next frame that has been acquired from array 12 and stored in memory 30 (101).

In edge filter analysis 116, DSP 24 filters out sensors 14 producing red signals 22 due to "edge effects" of array 12. Next, test 120 is performed on the red signals 22. Test 120 includes a continuity and size test 124, and a ratiometric test 128, which are used in combination to determine the pressure signature defined by red signals 22, and compare the pressure signature to characteristics of pressure signatures of the normal and potentially foreign tissue structures discussed above. Tests 124, 128 are described in detail below, but briefly are:

Continuity and Size Test 124—DSP 24 determines whether pressure sensors 14 that produce red signals 22 are contiguous with each other in array 12 to define a relatively large region, or are instead dispersed in smaller regions throughout the array. Test 124 also determines whether the large region predominates other, smaller regions of red signals.

Ratiometric Test 128—DSP 24 determines the difference between the highest amplitude red signal 22 in the frame and the lowest amplitude red signal 22 in the frame by taking the ratio between these signals, and compares the ratio to a threshold. This test determines whether the pressure signature defined by red signals 22 is peaked or is flat.

Tests 124, 128 are performed sequentially on red signals 22. If a test 124, 128 is passed, the next test in the sequence is performed; if either test 124, 128 fails, DSP 24 clears the frame from memory 30 and resets sequential counter (112), and analyzes next frame (101).

If both tests 124, 128 pass, this provides an initial indication that one or more suspicious (e.g., foreign) regions have been identified (130). (Conversely, the failure of any test 110, 124, 128 indicates (114) that the frame does not identify a suspicious region.) DSP 24 creates a map of the suspicious region or regions in the frame based on the locations in array 12 of the sensors 14 which have produced red signals 22, and stores this map in memory 30 (132). In addition, DSP 24 increments a sequential frame counter (134). Before proceeding with additional tests, DSP 24 obtains five consecutive frames that have passed tests 110, 124, 128, and uses the frame counter to monitor the consecutive number of frames that have passed tests 110, 124, 128. When the sequential frame count exceeds a selected count N (e.g., 5) (136), DSP 24 performs test procedure 140 on red signals 22 in the N successive frames; otherwise DSP 24 acquires the next frame to test.

Test sequence 140 augments tests 110, 124, and 128 by adding a level of specificity to test procedure 100 to help reduce the possibility of a "false positive" result (i.e., an indication by device 10 that a normal tissue structure is a potentially foreign tissue structure). Test 140 includes a pressure profile test 142 and a motion analysis test 144, which are used to determine whether red signals 22 define an approximately spherical shape in three dimensions, and whether areas of suspicion are moving in patterns which are consistent with the motion of the sensor head 55. Tests 142 and 144 are described in detail below, but briefly are:

Pressure Profile Test 142—DSP 24 determines the steepness of the edges, the ratio of the overall height to base of the suspicious region, and the degree of curvature along selective two dimensional cross-sections of the pressure signatures.

Motion Analysis Test 144—DSP 24 determines if suspicious regions remain in one place or if they move from one side of the frame to the other over successive frames. Test 144 also determines if the suspicious regions are moving in patterns which are consistent with the motion of sensor head 55.

Tests 142 and 144 are performed sequentially on suspicious signals 22, but do not produce binary (e.g., "pass" or "fail") outcomes. Instead, the outcomes of tests 142, 144 indicate the degree of correspondence between the characteristics of the underlying tissue structures and those of potentially foreign tissue structures. The outcomes of test 142, 144 are subjected to so-called "fuzzy logic" analysis 146. In fuzzy logic analysis 146, DSP 24 evaluates and weighs the outcomes of each of the previous tests 142, 144 and determines a "degree of membership" of each underlying tissue structure in a class of foreign tissue structures. Based on the determined degree of membership, DSP 24 decides whet-her or not test procedure 100 has detected a foreign structure such as a lump. If a lump has been found, DSP 24 illuminates red LED 40 (FIG. 1) and triggers audio circuit 50 to switch its output from the humming tone to a high pitch alarm tone (148). Otherwise, if no suspicious structure is found (114) DSP 24 clears the tested frames from memory 30 and resets sequential counter (112), and analyzes the next frame acquired by array 12 (101).

Figure 4A:
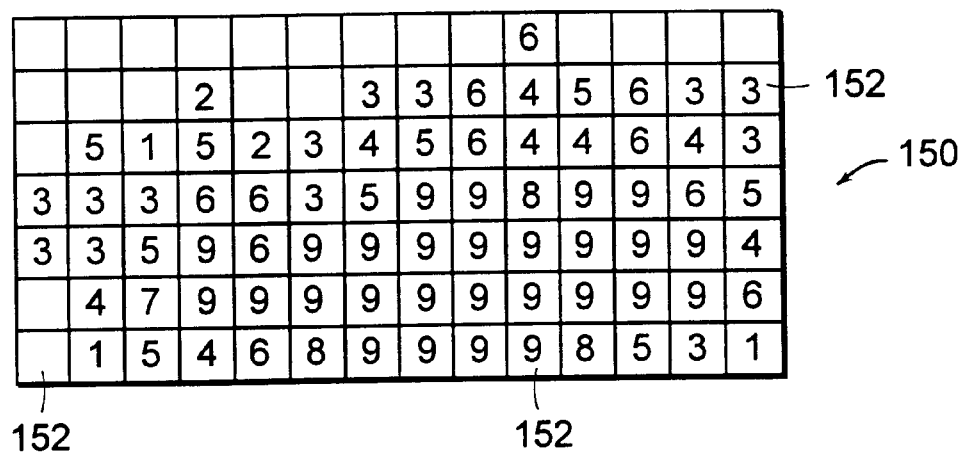
FIGS. 4A and 4B show pressure signals and a pressure signature, respectively, obtained by the tissue examination device of FIG. 1 for a rib.
Figure 4B:
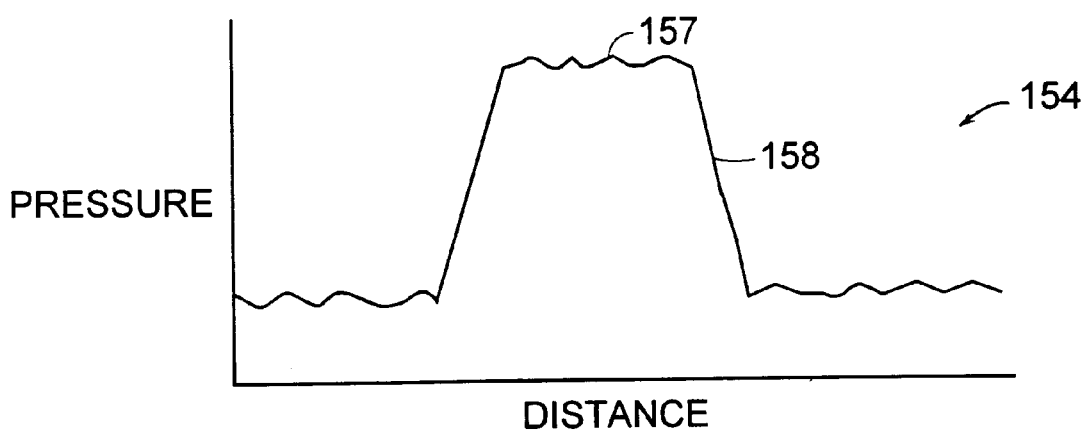

FIG. 4A shows a frame 150 of red signals 22 obtained for a rib. Frame 150 is illustrated as an orthogonal grid of locations 152, each of which corresponds to a storage location 27 in the memory area 26a–26n in which frame 150 is stored. Those locations that contain signals 22 which do not exceed the pressure threshold applied in test 110 are shown empty in FIG. 4A for clarity. The numbers (1–9) shown in the other storage locations 152 indicate the relative pressure values. The locations with the highest pressure values are assigned level "9;" level "1" locations 152 are those with the lowest pressure value. (The image produced by visual display 54, FIG. 1, might display the various values shown in FIG. 4A in different colors to help the user visualize the pressure profile.) The pressure signature 154 that corresponds to frame 150 is shown in FIG. 4B as a curve of pressure (corresponding to the levels of suspicious signals 22) vs. distance. Because a rib is anchored to the skeletal system, when the user presses sensor array 12 against tissue that overlies the rib, the immobile rib effectively "pushes back" against sensors 14. As a result, the pressures detected by pressure sensors 14 above the rib tend to be large (e.g., level "9"), and pressure signature 154 has a correspondingly large amplitude. Moreover, when the detected pressures are viewed spatially, it is seen that the large amplitude pressures define a relatively flat plateau 157, and the edges 158 of pressure signature 154 are sharply defined and rise relatively rapidly to plateau 157 at the boundaries of the rib. Finally, if the rib is sensed by placing array 12 parallel to the rib, or equivalently if distance coordinate is aligned to the long axis of the 2-D shape, pressure signature 152 will be elongated due to the elongation of the rib.

Figure 5A:
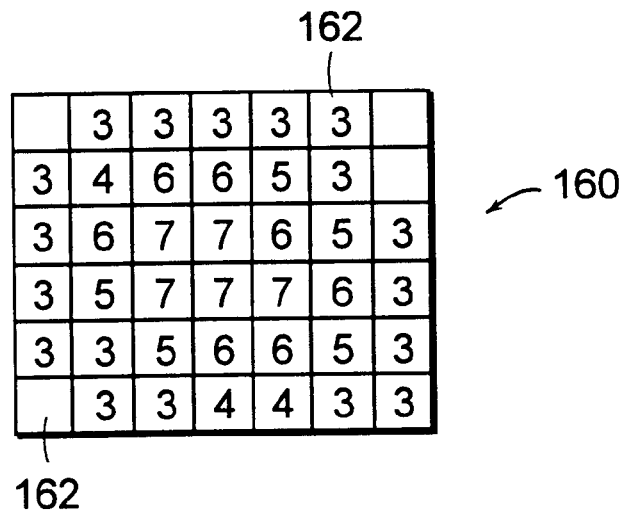
FIGS. 5A and 5B show pressure signals and a pressure signature, respectively, obtained by the tissue examination device of FIG. 1 for a nipple.
Figure 5B:
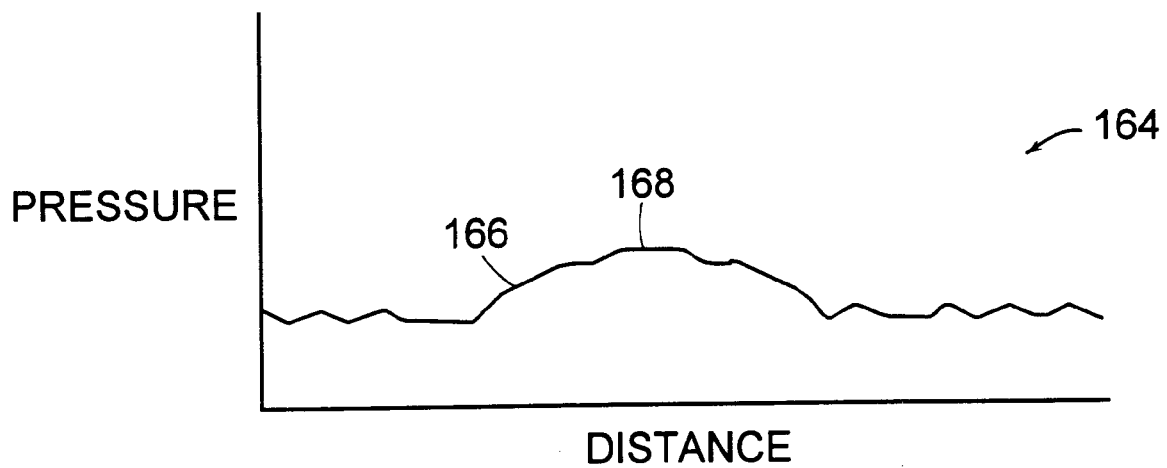

FIGS. 5A and 5B respectively show a frame 160 of suspicious signals 22 obtained for a nipple, and the corresponding pressure signature 164. The nipple and the surrounding areola are relatively soft, although the edge of the areola has a relatively distinct boundary which can be detected by pressure sensors 14. Accordingly, the amplitudes of suspicious signals 22 at locations 162 in frame 160 are relatively low (particularly compared with the levels obtained for harder structures, such as the rib discussed above). In this example, the levels of suspicious signals range from 3 to 7. The amplitude of pressure signature 164 changes gently, and pressure signature 164 has relatively gradually sloped edges 166 and a crest 168 that is relatively flat, with no peaks.

The nipple can also be identified by using a scanning examination technique. Scanning involves the user pressing sensor array 12 against the skin and moving array 12 in a circular path. In this approach, the skin will remain somewhat stationary against array 12 as pressure sensors 14 are moved over the underlying tissue. In the scanning technique, the nipple and any abnormalities on the skin (such as moles and pimples) will move with the skin, because the user is pressing array 12 against the skin while scanning. In this case, when signals 22 are analyzed on a frame-by-frame basis, the nipple will appear stationary while the underlying tissue will be seen to move.

Figure 6A:
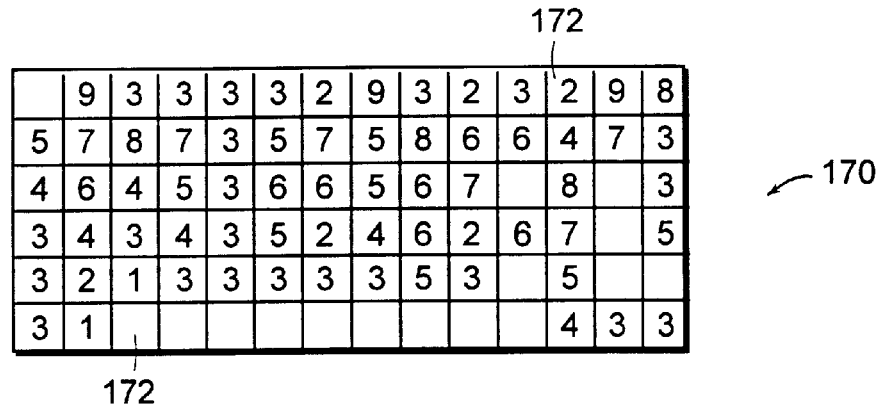
FIGS. 6A and 6B show pressure signals and a pressure signature, respectively, obtained by the tissue examination device of FIG. 1 for an inframammary ligament.
Figure 6B:
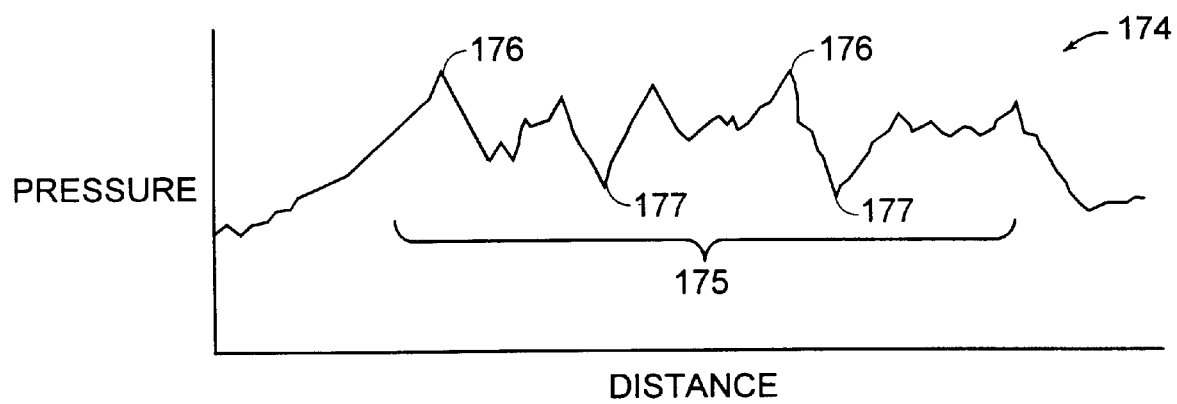

FIGS. 6A and 6B illustrate a frame 170 of locations 172 in which red signals 22 are obtained for the inframammary ligament, and the corresponding pressure signature 174. The inframammary ligament is a relatively wide structure that runs along the base of the breast and provides support for the breast tissue. Accordingly, the pressure signature of the inframammary ligament is relatively wide and long 175 (depending upon the orientation of array 12). Moreover, the pressure levels detected by sensors 14 are somewhat randomly distributed in pressure signature 174. That is, sensors 14 that detect high pressure values 176 and sensors 14 that detect low pressure values 177 are dispersed throughout array 12. Thus, there is no contiguous region of high pressure beneath array 12 that would indicate a foreign tissue structure (e.g., a pathogenic body). This random pressure distribution, as well as large width 175, allow pressure signature 174 to be distinguished from other pressure signatures.

Figure 7A:
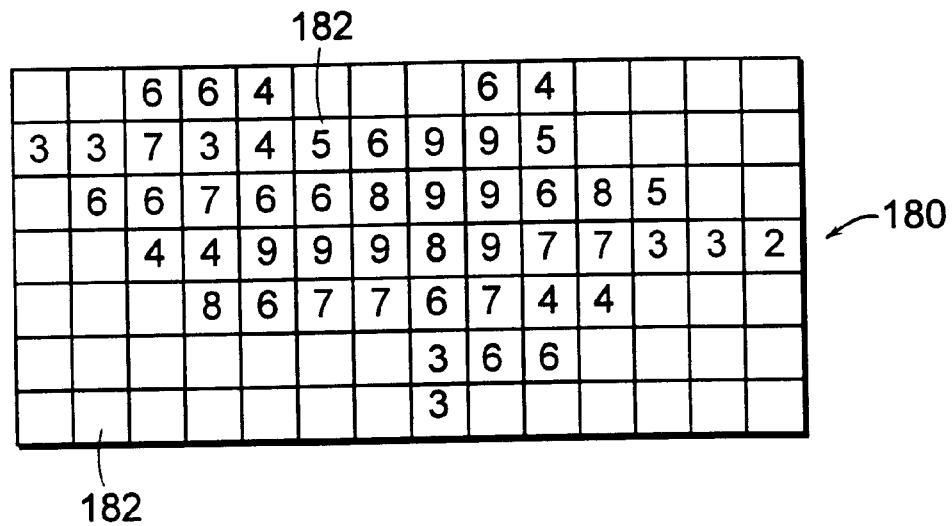
FIGS. 7A and 7B show pressure signals and a pressure signature, respectively, obtained by the tissue examination device of FIG. 1 for a cyst.
Figure 7B:
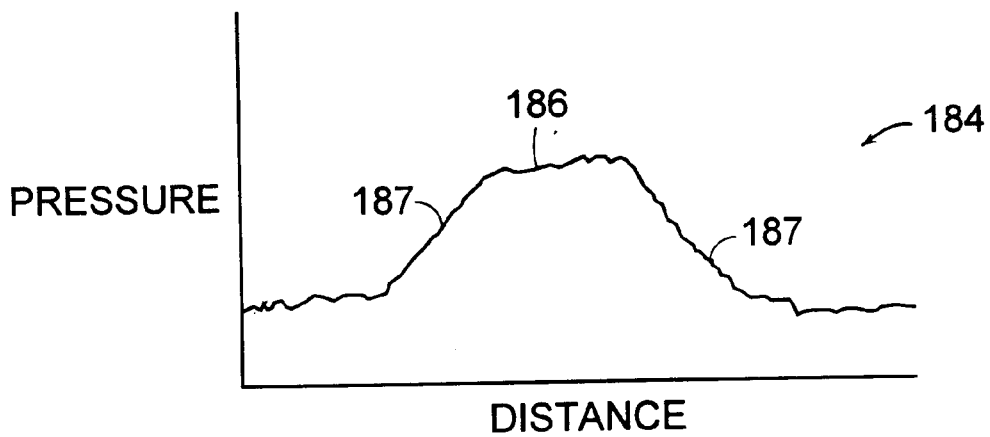

The pressure signature of a cyst is a function of the hardness of the cyst. A hard cyst is indistinguishable from a solid mass (discussed below). The pressure signature 184 of a soft cyst is shown in FIG. 7B (the corresponding frame 180 of locations 182 in which red pressure signals 22 are stored is shown in FIG. 7A). A soft cyst has a correspondingly soft (i.e., low amplitude) pressure signature 184 in which an area 186 of relatively high pressure is distributed over the central region of the cyst. In this regard, one can imagine that array 12 is flattening the cyst as the user presses against the breast, thereby creating central area 186 of large pressure.

Cysts have discrete boundaries, which is another characteristic that enables pressure signature 184 of a soft cyst to be distinguished from the pressure signatures of other structures. A cyst is essentially a fluid filled body, and the fluid pressure within the cyst tends to make it circular (in two-dimensions) with well-defined edges. Accordingly, as array 12 moves across such an edge, the pressure drop is much more dramatic than with, for example, a diffuse tumor, which would have less discrete boundaries. The well-defined edges of the cyst are reflected in pressure signature 184 by medium differential pressures at edges 187.

Figure 8A:
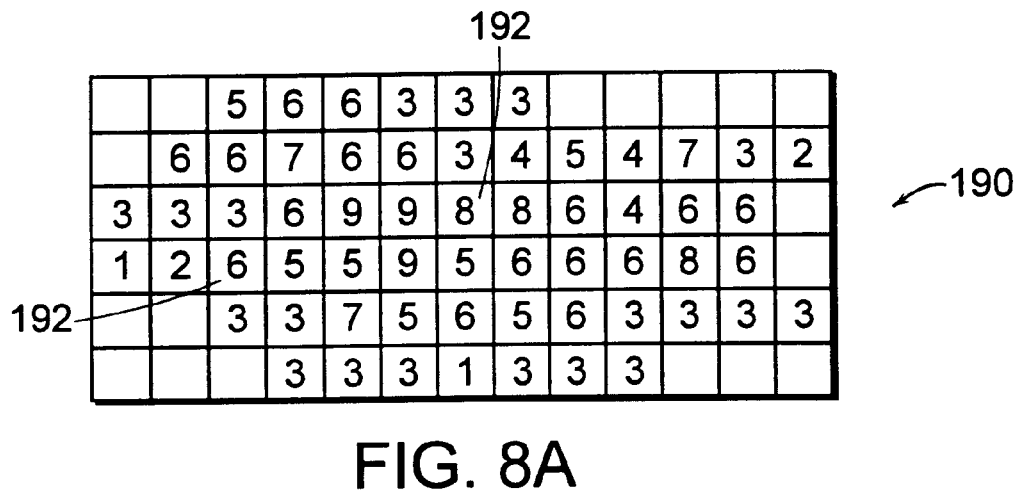
FIGS. 8A and 8B show pressure signals and a pressure signature, respectively, obtained by the tissue examination device of FIG. 1 for a solid mass.
Figure 8B:
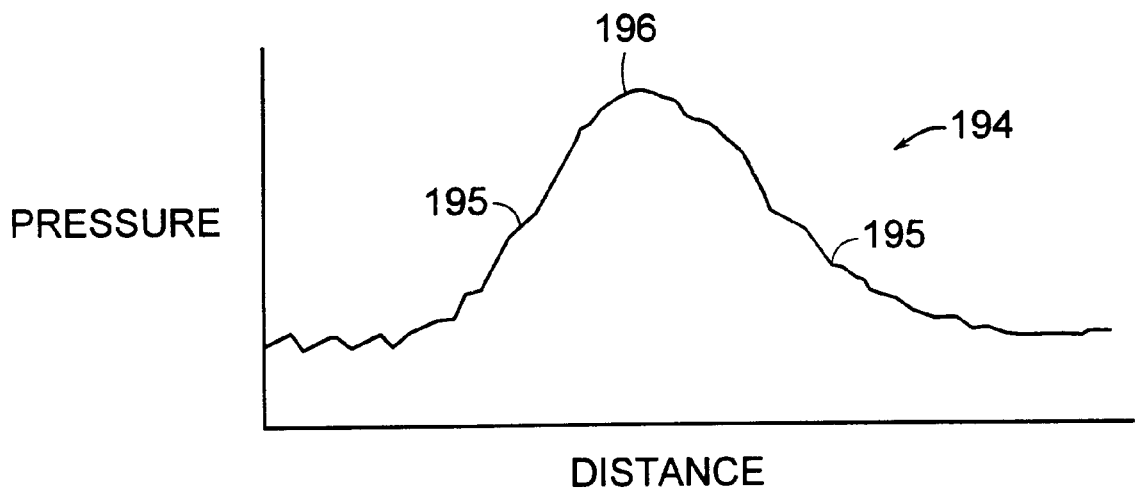

Referring also to FIGS. 8A and 8B, a benign solid mass typically has discrete boundaries much like a cyst. A cyst is often indistinguishable from a solid mass by manual palpation. Indeed, red signals 22 obtained from a benign solid mass define a pressure signature 194 (FIG. 8B) which is similar to a cyst pressure signature. (A frame 190 of locations 192 in which such red signals are stored is shown in FIG. 8A.) For example, pressure signature 194 has relatively sharp edges 195 (which correspond to the discrete edges of the mass) and a central region 196 with a large amplitude. But unlike the pressure signature of a soft cyst, central region 196 of pressure signature 194 (which corresponds to the pressures produced by pressing array 12 against the high-elevation areas of the mass) is relatively small.

Unlike a rib, which as discussed is anchored to surrounding tissue and thus "pushes back" against the pressure applied by the user, cysts and benign solid masses are relatively free to move in response to the user-applied pressure. Accordingly, although cyst pressure signature 184 and solid mass pressure signature 194 have distinct edges (187, 195, respectively), the edges are not as well-defined as the edges 158 of a rib pressure signature (FIG. 4B). This difference provides one way of distinguishing the pressure signatures of cysts and benign solid masses from that of a rib.

One way in which a carcinoma differs from a cyst or a benign solid mass is that a carcinoma typically is diffuse and infiltrates surrounding tissue. As a result, the carcinoma is anchored to the surrounding tissue and does not move like a cyst or benign mass in response to palpation. Accordingly, the pressure signature of a carcinoma, like that of a rib, is harder—that is, has larger amplitudes—than that of either a cyst or a benign solid mass. Unlike a rib, however, the edges of a carcinoma are not discrete, and thus the pressure level at the boundaries of the carcinoma does not decrease as sharply as that at the edges of a rib (see FIG. 4B).

Referring again to FIG. 3, test procedure 100 enables DSP 24 to distinguish between the pressure signatures discussed above by analyzing various characteristics of the signatures. Based on the results of the various tests performed in test procedure 100, DSP 24 determines whether a tissue structure detected by pressure sensor array 12 is a normal tissue structure (such as a rib, the inframammary ligament, or the nipple) or a potentially foreign structure (such as a cyst, a benign solid mass, or a carcinoma).

Figure 9:
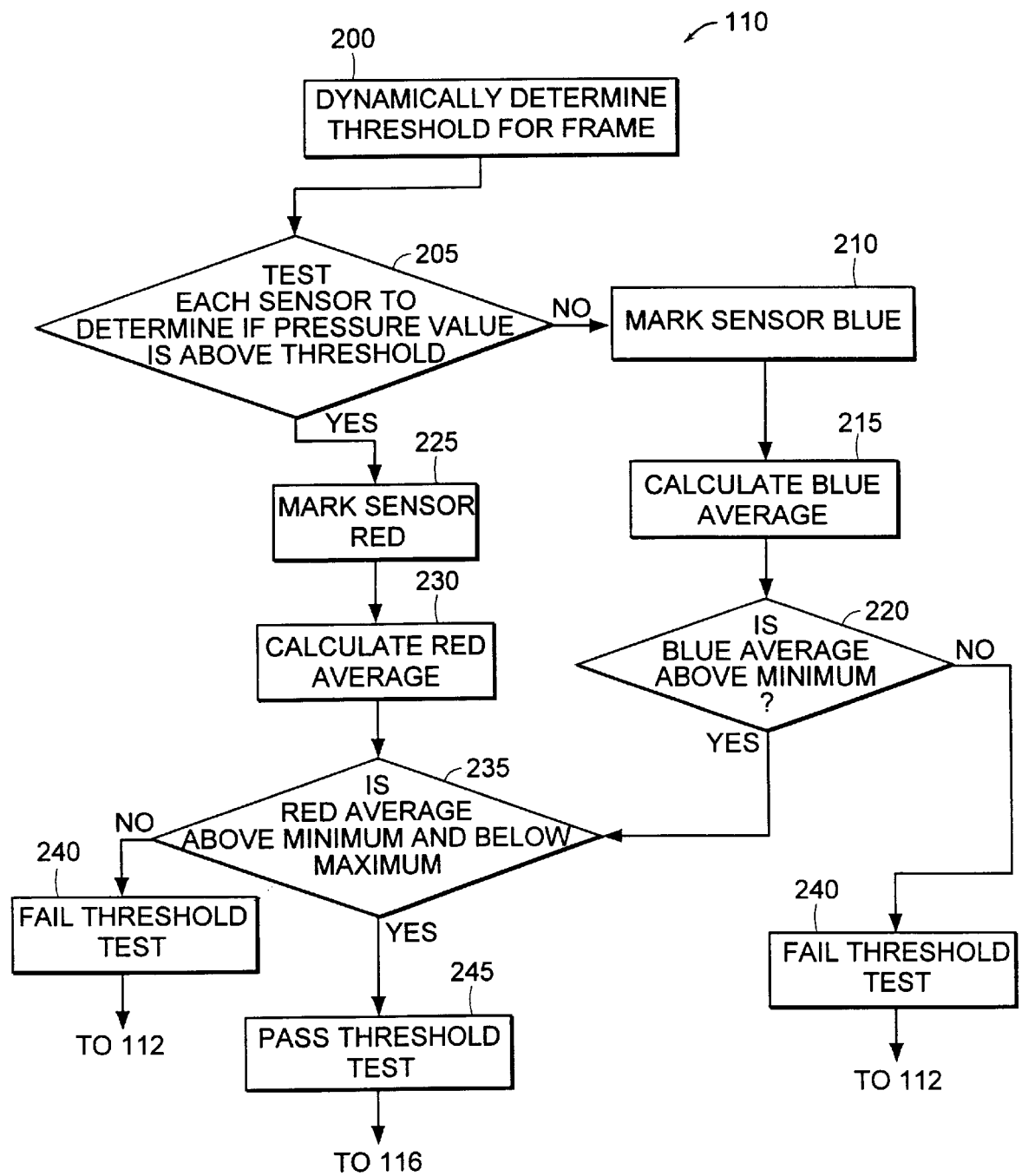
FIG. 9 is a flow chart of a threshold test performed during the operation of the tissue examination device of FIG. 1.

Referring also to FIG. 9, threshold test 110 is used to determine whether a frame includes a sufficient number of red—that is, suspicious—signals 22. DSP 24 derives the threshold dynamically for each frame by determining the average pressure detected by all sensors 14 in array 12, and multiplying the average by an empirical value (the "red/blue factor") (200). (The average pressure for a frame is obtained by adding the pressure values detected by sensors 14 and dividing the result by the number of sensors 14 in array 12.)

At step 205, DSP 24 compares the pressure value of each location in the frame (i.e., the amplitude of signal 22 produced by each sensor 14 in array 12) with the dynamic threshold obtained in step 200. If the pressure value produced by a sensor 14 is above the dynamic threshold, the location of the sensor 14 is marked "red" (225). If the pressure value is below the dynamic threshold, the location of the sensor 14 is marked "blue" (210). As discussed below, signals 22 from red sensors 14 are evaluated differently than signals 22 from blue sensors 14.

In steps 215 and 230, respectively, DSP 25 calculates the average pressure values for the blue sensors 14 and red sensors 14. In each case, this is done by adding the pressure values produced by the sensors and dividing the result by the number of blue sensors 14 or red sensors 14, respectively. In step 220, DSP 24 compares the average pressure value of the blue sensors 14 with a predetermined minimum pressure value (e.g., 0.03 psi). If the average pressure value of the blue sensors 14 is below this minimum amplitude, this indicates that the background (i.e., blue) structures in the frame are being pressed upon too lightly for the frame to be regarded as valid (despite the frame having passed initial test 102). Accordingly, threshold test 110 fails, and no further testing on this frame occurs (240). DSP 24 clears the frame from memory 30 and resets frame counter (112 FIG. 3), and acquires next frame for testing (101).

DSP 24 also determines whether the average pressure value of the red sensors 14 (step 230) is within a selected range of amplitudes (235). If the red average is below the range (e.g., below 0.1 psi), this indicates that the underlying structure likely is normal tissue; on the other hand, if the red average exceeds the range (e.g., is above 4 psi), this indicates that the underlying structure is bone. If the red average is within the range (and the blue average is above the minimum amplitude applied in step 220), threshold test 110 passes. This means that the underlying structure is considered to be suspicious, and DSP 24 performs edge filtering 116 on the frame. Otherwise, the frame fails (240) threshold test 110 and no further testing on this frame occurs. In this case, DSP 24 proceeds to step 112 (FIG. 3) and obtains the next frame (101) for testing.

Figure 10:
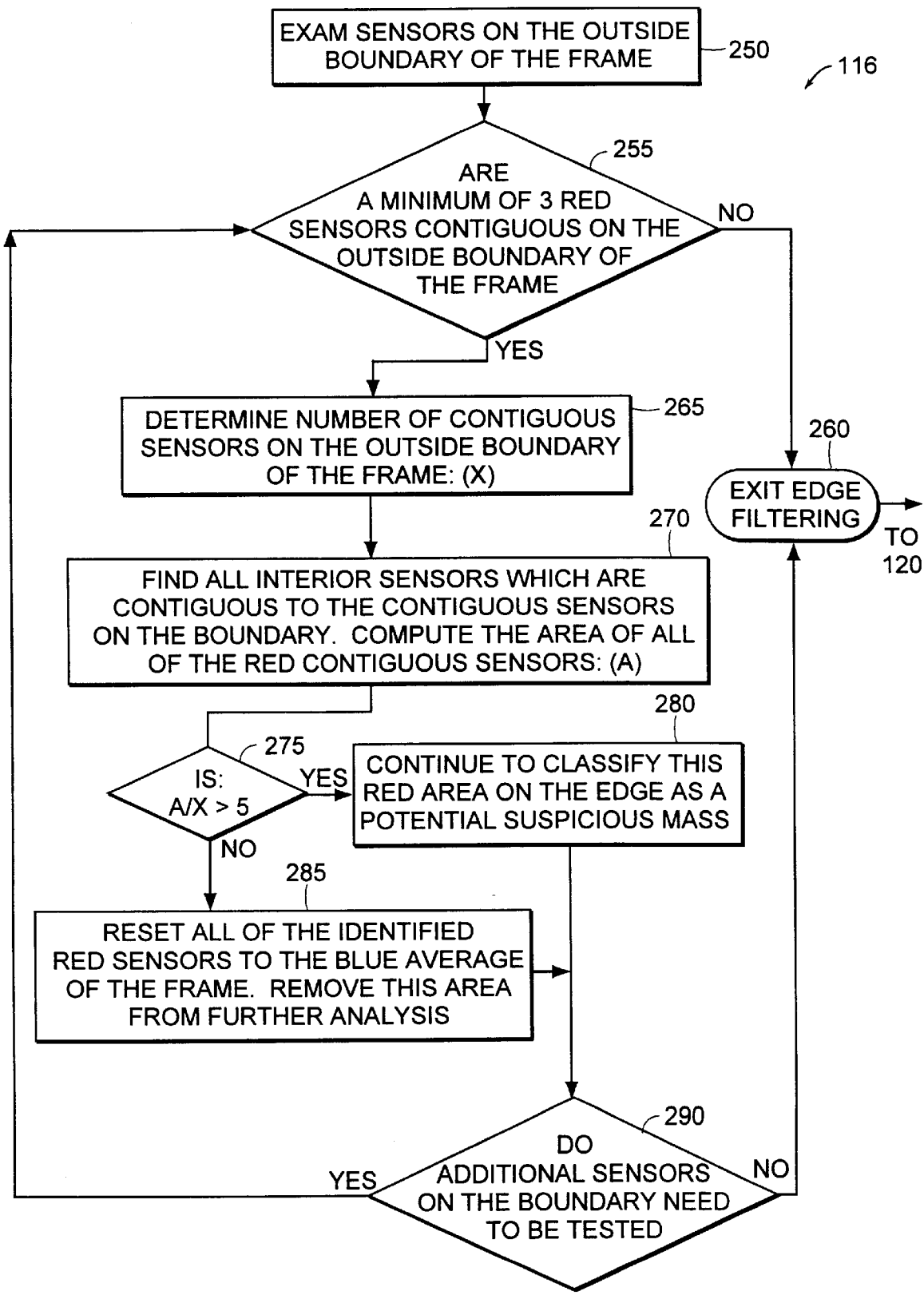
FIG. 10 is a flow chart of an edge filter analysis performed during the operation of the tissue examination device of FIG. 1.

FIG. 10 is a flow chart of edge filter analyses 116. The purpose of edge filtering 116 is to determine whether red signals 22 produced by sensors 14 at the edges of array 12 are valid (i.e., accurately represent potentially suspicious underlying structures), or are instead the results of "edge effects" caused by the user applying excessive pressure to the edge of array 12. Thus, the first step (250) is to examine the signals 22 produced by sensors 14 and the periphery of array 12 (i.e., signals 22 on the outside boundary of the frame) to determine whether such signals 22 are "red" or "blue." Then, DSP 24 sequentially examines signals 22 around the periphery of the frame to determine whether a minimum of three contiguous sensors 14 have produced red signals 22 (255). If not, the edge effects (if any) are not considered to be significant, and DSP 24 proceeds to test 124 (260).

If at least three contiguous sensors 14 which have produced red signals are found, DSP 24 continues to examine sensors 14 along the edge of array 12 until a sensor 14 which has generated a blue signal is encountered, and the total number "X" of contiguous red sensors 14 are counted (265). At step 270, DSP 24 searches for sensors 14 in the interior of array 12 that: (1) produce red signals 22, and (2) are adjacent to the contiguous red sensors 14 on perimeter of the frame or to each other. The interior sensors are those sensors that are adjacent (vertically, horizontally, or diagonally) to the contiguous red sensors 14 on the perimeter. DSP 24 then counts the total number of contiguous red sensors 14 ("A") by adding the number of contiguous red sensors 14 located in interior of the frame to the number of contiguous red sensors 14 found on the perimeter of the frame in step 265.

By calculating the ratio of A/X, DSP 24 determines the relationship between the red area beneath array 12 and the red area at the edge of array 12. If this ratio exceeds an empirical value (e.g., 5) (275), this indicates that the overall area of the suspicious region defined by red signals 22 is significant relative to the edge component of that area, and therefore that the edge component warrants continued testing as a part of the suspicious region. Accordingly, DSP 24 continues to classify the red signals 22 on the edge as a potential suspicious region, and does not change these values as stored in the frame in memory 30 (280).

If, however, the ratio is five or less, this indicates that the red signals 22 at the periphery are due to user-induced edge effects. DSP 24 resets the pressure values of the red sensors 14 on the edge to an amplitude below the dynamic threshold for the frame determined in step 200 of threshold test 110 (FIG. 9). For example, the pressure values are reset to the average pressure value of the blue sensors 14 determined in step 215 of threshold test 110. By this filtering process, DSP 24 is able to disregard some red sensors 14 that are false positives and reset them to blue, thereby removing them from further analysis (285).

DSP 24 then determines whether there are other contiguous red sensors 14 located on perimeter of the frame that should be analyzed (290). If there are such sensors 14, DSP 24 returns to step 255. If there are no other contiguous red sensors 14 to be examined, DSP 24 exits (260) edge filter analysis 116 and proceeds to test sequence 120.

Figure 11:
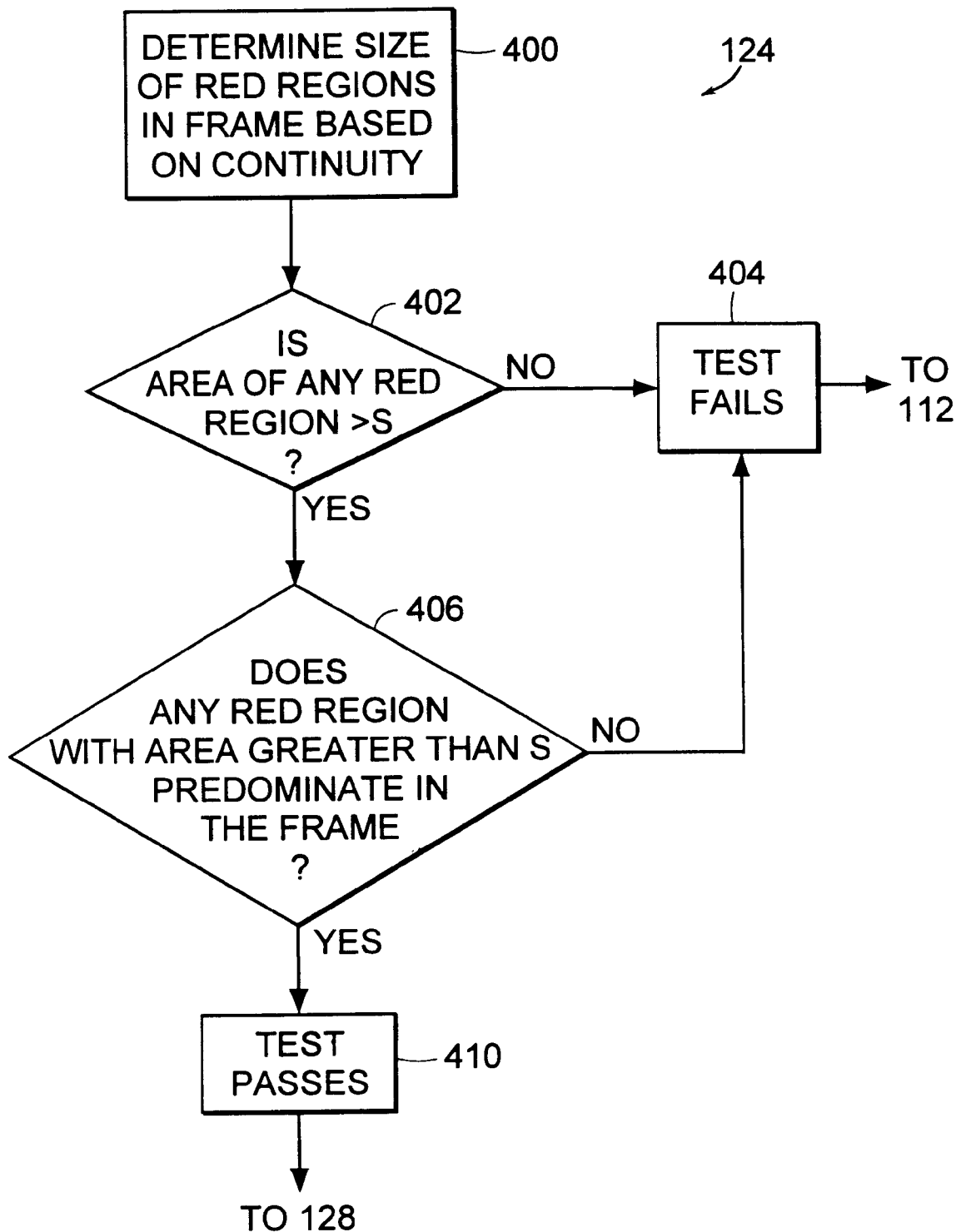
FIG. 11 is a flow chart of a size and continuity test performed during the operation of the tissue examination device of FIG. 1.

Referring to FIG. 11, the first test in sequence 120 is continuity and size test 124. In continuity and size test 124, DSP 24 first determines the size (e.g., area) of each suspicious region in the frame (400). This is done by identifying the relative locations in array 12 of pressure sensors 14 that generated red signals 22 (i.e., signals 22 exceeding the pressure threshold applied in test 110), and determining whether or not those sensors 14 are located contiguously to each other. That is, DSP 14 determines whether each pressure sensor 14 that generates a red signal 22 is located adjacent (either horizontally, vertically, or diagonally) to another sensor 14 that generates a red signal 22, or is instead surrounded by sensors 14 which produced blue signals (i.e., signals 22 below the pressure threshold). DSP 24 determines the area of each suspicious region simply by counting the number of contiguous sensors 14 overlying the region that produce red signals 22. It will be appreciated that a frame may have more than one such suspicious region.

Next, DSP 24 determines whether any of the suspicious regions has an area that exceeds a minimum size ("S") (402). For example, minimum size S corresponds to 25 contiguous red sensors 14. If none of the suspicious regions meet the size threshold, test 124 fails (404), and DSP 24 proceeds to step 112 (FIG. 3). In this way, DSP determines whether pressure sensors 14 that generate red signals 22 are sufficiently grouped together (i.e., are contiguous) in array 12 to indicate that the pressure signature corresponds to a foreign tissue structure, or are instead dispersed throughout array 12 (which indicates the presence of normal breast tissue or represents dispersed variations in breast tissue stiffness, such as are caused by small cysts, e.g., fibrocystic tissue).

If at least one suspicious region in the frame meets the size threshold of step 402, DSP 24 examines the size of this suspicious region relative to the aggregate size of the suspicious (i.e., red) regions in the frame to determine the degree of prominence of the suspicious region (406). This is done by comparing the area of each large suspicious region (i.e., each region that has an area of S or more) with the aggregate area of that region and all nonadjacent suspicious regions in the frame with areas less than S. If the ratio between these areas is 70% or more, the large suspicious region is deemed to predominate the other suspicious regions in the frame, thereby indicating that the large region is a foreign structure. In this case, test 124 passes (410), and DSP 24 proceeds to ratiometric test 128. If no large regions predominate, test 124 fails (404), and DSP proceeds to step 112 (FIG. 3).

For example, suppose a given frame contains the following three contiguous regions of red sensors 14: region (R) having twenty-five or more contiguous red sensors, and regions (R') and (Z) containing less than twenty-five contiguous red sensors each. This frame passes step 402 because of the size of region R. Accordingly, DSP 24 proceeds to step 406 and takes the ratio of:

$$\frac{R}{R + R' + Z}$$

If this ratio is seventy percent or more, the frame passes continuity and size test 124; if not, test 124 fails.

If more than one region in a frame passes step 402, step 406 is performed separately for each such region. For example, assume from the previous example that regions R and R' both have 25 or more contiguous red sensors, thereby passing test 402. In this case, DSP 24 will calculate two ratios:

$$\frac{R'}{R' + Z} \text{ and } \frac{R}{R + Z}$$

If either ratio is seventy percent or higher, the frame passes continuity and size test 124; otherwise, test 124 fails.

The next test in sequence 120 is a ratiometric test 128, which is performed to determine whether the pressure signature is flat (like those of normal breast tissue, the inframammary ligament, or a nipple) or is peaked (as are the pressure signatures of the cysts, benign solid masses, and carcinomas). DSP 24 performs test 128 by determining a ratio between the highest amplitude and the lowest amplitude of the red signals 22 in the frame. DSP 24 compares the ratio to a predetermined empirical threshold ratio (e.g., 1.7). If the threshold is exceeded, DSP 24 determines that the pressure signature is peaked, and ratio- metric test 128 is deemed to have passed. If the ratio is less than the threshold, the pressure signature is determined to be too flat to correspond to a potential foreign structure, and test 128 fails. In this case, DSP 24 clears the frame from memory 30, resets a sequential counter (112), and proceeds to next frame (101).

Referring again to FIG. 3, if a frame passes test procedure 100 through test 128, the suspicious region or regions in the frame are deemed to correspond to a potentially foreign tissue structure (130). Because of the size of sensors 14 and their spacing in array 12, the foreign structure may be as small as 1 cm in diameter, and thus it will be appreciated that device 10 is highly sensitive.) DSP 24 stores a map of each suspicious region in memory 30 for further analysis in tests 140, 146 (132). To reduce the risk of a false positive output, before subsequent tests 140, 146 are performed, a minimum number (N) of consecutive frames must pass test 128 without interruption by a frame that fails one of tests 110, 124, or 128. DSP 24 increments a frame counter (134) when a frame passes test 128. If the frame count exceeds N (136), DSP 24 proceeds to test sequence 140; if not, DSP 24 analyzes the next frame acquired by array 12 (101). The frame counter is reset to zero if any frame fails any test 110, 124, 128.

Figure 12:
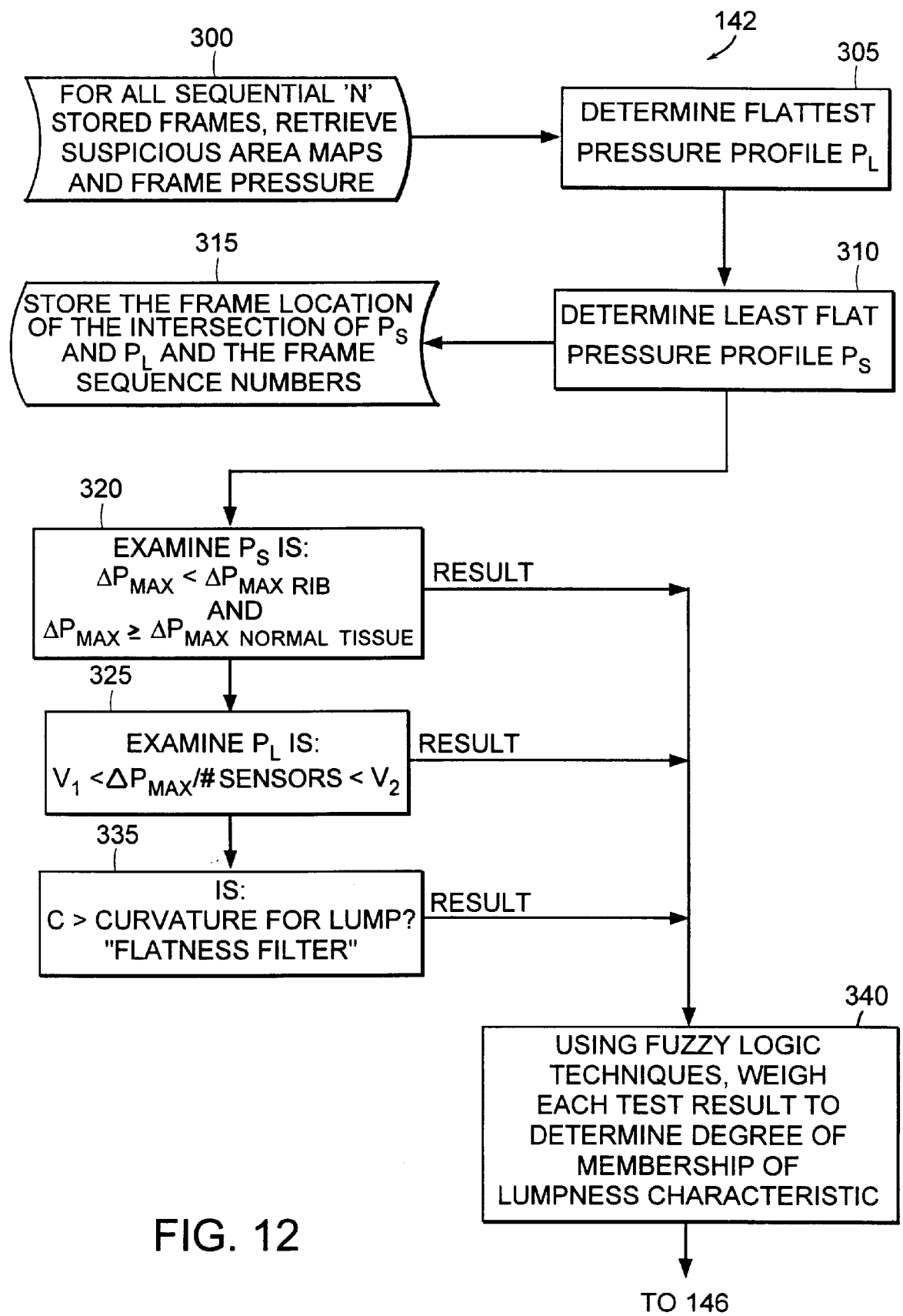
FIG. 12 is a flow chart of a pressure profile test performed during the operation of the tissue examination device of FIG. 1.

FIG. 12 is flow chart of the first test in sequence 140, pressure profile test 142. Test 142 is a 3-D (three-dimensional) test in which DSP 24 analyzes the amplitudes of red signals 22 to determine whether the pressure signature of the tissue structure is approximately lump-like in three dimensions. For example, test 142 enables DSP 24 to determine whether the central region of the pressure signature is relatively large (like that of a soft cyst, FIG. 7B) or is small (like that of a solid mass, FIG. 8B). Due to their somewhat spherical shapes, foreign structures (such as cysts, benign solid masses, or carcinomas) induce pressure signals 22 with amplitudes that increase progressively as pressure is sampled from the periphery of the structures to their center. Accordingly, in test 142 DSP determines the edge profile, the relative stiffness, and the relative curvature of the underlying structure based on how the amplitudes of suspicious signals 22 change from the periphery of the structure toward the center of the structure. DSP 24 evaluates the edge profile to determine whether it is extremely sharp (which indicates that the structure may be a rib, rather than a lump) or is more moderate. DSP 24 also determines whether the structure's stiffness and curvature are more indicative of a lump than of a normal tissue structure.

In step 300, for each of the N sequential frames that have passed test 128, DSP 24 retrieves the suspicious region maps that were stored in memory 30 in step 132 (FIG. 3), and the average pressure for that frame which was calculated during step 200 (FIG. 9). DSP 24 then analyzes each suspicious (i.e., red) region to derive a pair of pressure profiles along the two dimensions of the suspicious region that are the most flat and the least flat, respectively. This is done as follows. First, DSP 24 plots a line segment of sensors 14 in any direction through the suspicious region. DSP 24 then successively examines the values of the pressure signals 22 produced by the sensors 14 along the line segment to determine the absolute value of the difference (ΔP) between the signals produced by each adjacent pair of sensors along the line segment. DSP 24 then determines the average change in pressure ($\Delta P_{AVG}$) along the line by summing the ΔP calculations and dividing the result by the number of ΔP calculations in the line segment. The average pressure change ($\Delta P_{AVG}$) is then normalized by dividing it by the frame average pressure (obtained in step 200, FIG. 9). The resultant value (C) provides an indication of the relative curvature of the suspicious region along the line segment— the lower that C is, the flatter the suspicious region is along that dimension.

After DSP 24 has obtained a curvature value C along a given dimension of the suspicious region, DSP 24 rotates the line segment plotted through the suspicious region by a selected amount (e.g., 10°) to examine an incrementally different dimension. DSP 24 calculates a curvature value C for that dimension in that same manner as described above. DSP 24 repeats these steps until it has rotated the line segment by 180°. For example, consider that the initial line segment is plotted vertically through the suspicious structure (i.e., at 0°). DSP will obtain curvature values C for that line segment as well as for line segment plotted at increments of 10° until the line segments have been rotated by 180°.

DSP 24 examines the curvature values C obtained during the iterations of the line segments and retains in memory the dimensions that correspond to the lowest and highest curvature values C, respectively. When the iterations are completed, the dimension having the lowest curvature value C is designated as pressure profile $P_L$, that is, the flattest dimension of the suspicious region (305). Likewise, the dimension having the highest curvature value C is designated as pressure profile $P_S$, that is, the least flat dimension of the suspicious region (310). Typically, although not always, $P_S$ is orthogonal to $P_L$. DSP 24 then determines the location in the frame of the intersection between $P_S$ and $P_L$, and stores (315) this location in memory (along with a sequence number or the like that identifies the frame). Note that if the frame contains more than one suspicious region, multiple intersection locations will be stored.

DSP 24 then examines pressure profiles $P_S$ and $P_L$ of the suspicious regions to evaluate the edge profile, relative stiffness, and "flatness" of the each suspicious region. In step 320, DSP 24 evaluates the edge profile by examining the absolute value of the maximum pressure signal change from sensor 14 to sensor 14 along $P_S$ ($\Delta P_{MAX}$) to determine whether it is within a selected range that is bounded by empirically-determined $\Delta P_{MAX}$ values for normal tissue ($\Delta P_{MAX\ NORMAL\ TISSUE}$) (e.g., 0.5 psi) and for very stiff objects ($\Delta P_{MAX\ RIB}$), such as a bony prominence (e.g., 1.0 psi). The underlying object is more likely to be a foreign tissue structure if $\Delta P_{MAX}$ is within the range. The result of step 320 is applied to "fuzzy logic" step 340, described below.

Next, in step 325, DSP 24 evaluates the stiffness of the suspicious region by examining $P_L$ for that suspicious region to determine whether difference between the highest and lowest pressure signals obtained along $P_L$ ($\Delta P_{MAX}$) (averaged by the number of sensors 14 along $P_L$) is within a range defined by a pair of empirical values ($V_1$, $V_2$). The empirical value at low end of the range ($V_1$) corresponds to values obtained from normal tissue or nonpalpable lumps; the empirical value at the upper end of the range ($V_2$) corresponds to values obtained from a bony prominence. The result of step 325 (i.e., the degree to which $\Delta P_{MAX}$ averaged by the number of sensors in $P_L$ falls within the range) is applied to fuzzy logic step 340.

In step 335, DSP 24 applies a "flatness filter" to pressure profile $P_L$ to compare the curvature of the suspicious region along $P_L$ to an empirically determined curvature for a foreign tissue structure such as a lump. More specifically, DSP compares the curvature value C associated to $P_L$ and an empirically determined curvature value for a lump. The degree to which C exceeds the empirical curvature (if at all) is reported to fuzzy logic step 340.

At step 340, DSP 24 applies so-called "fuzzy logic" techniques (also known as "soft thresholding") to weigh the results of steps 320, 325, 335. This technique is a neural network concept that develops parameters of imprecise measurements. DSP 24 weighs the edge profile, stiffness, and curvature as determined in steps 320, 325, 335 and develops a "degree of membership" outcome ranging from 0 to 1 of the lumpness characteristic of the suspicious region in a class of foreign tissue structures (i.e., the degree to which, based on the weighed results of steps 320, 325, 335 the suspicious region resembles a foreign tissue structure), and reports the result to test 146 (FIG. 3). DSP 24 weighs the results of steps 320, 325, and 335 equally, but alternatively could assign different weights to these results. DSP 24 then performs motion filter test 144.

FIG. 12 is a flow chart of a motion filter test 144 to determine how the center of mass (CM) of a suspicious region moves from frame-to-frame within a coordinate system defined by array 12. Test 144 also determines if the suspicious regions are moving in patterns which are consistent with the motion of the sensor head 55.

Initially, in step 355, DSP retrieves from memory 30 the locations of the intersections between $P_L$ and $P_S$ for the suspicious regions in the frame (recall that these locations were determined and stored in step 315 of pressure profile test 142). Each $P_{L–PS}$ intersection defines the center of mass (CM) of the corresponding suspicious region. DSP 24 then computes the distance that each CM moves over the sequence of frames by comparing the location of each CM in the first frame in the sequence with the location of the corresponding CM for the last frame in the sequence (360).

In step 365, DSP 24 determines whether the distance that each CM moves over the sequence of frames is within a selected range (in millimeters) between a minimum distance ($D_{MIN}$) and a maximum distance ($D_{MAX}$). This allows DSP 24 to determine whether the suspicious regions are stationary (if the amount of motion is less than $D_{MIN}$) or are moving by such an amount (greater than $D_{MAX}$) so as to indicate that the suspicious regions are random noise. The result of step 365 is sent to step 146.

DSP 24 then determines the relative motion of the sensor head 55 to detect the velocity with which the user is translating device 10 across the breast (375). This is done based on the velocity information provided by motion sensor 70 (FIG. 1). DSP 24 compares the frame-to-frame motion of each CM relative to the motion of the sensor head 55 across the breast to determine the rate at which each suspicious region is moving with respect to the velocity of device 10 across the breast (380).

For example, suppose the suspicious region is a cyst. DSP 24 first computes the trajectory of the center of motion of the cyst over the sequence of frames. Then, DSP 24 determines if the distance that CM moved is within the $D_{MIN}$–$D_{MAX}$ range to reject random signals. DSP 24 next determines velocity of device 10 as it is translated across the skin. Finally, DSP 24 compares the trajectory of the cyst with the relative motion of the sensor head 55. Because the cyst is mobile in the breast tissue, DSP 24 will determine, in step 380, that the motion of the cyst differs from that of sensor head 55 across the breast. In contrast, if the suspicious region is a rib or other stationary structure, it will appear to move at the same velocity as sensor head 55, which will be detected in step 380. The result of step 380 is applied to fuzzy logic step 146 (FIG. 3).

Referring again to FIG. 3, DSP 24 applies a fuzzy logic test 146 to the results of pressure profile test 142 and motion analysis 146. Test 146 is a neural network concept that develops parameters of imprecise measurements. In test 146, DSP 24 weighs the results of tests 140, 142 (assigning equal or unequal weights to tests 140, 142) and calculates a "degree of membership" ranging from 0 to 1 of the lumpness characteristics of the suspicious region.

Based on the results of test 146 (and hence of prior tests and analysis 110, 116, 124, 128, 142, 144, and 146), DSP 24 determines, with a high degree of certainty, whether the tissue detected by pressure sensors 14 is a normal structure or if the lumpness characteristics of the suspicious region warrants activating the alarm. In the latter case, DSP 24 illuminates red LED 40 and triggers the high pitch alarm tone (148). Otherwise, DSP 24 clears the frames from memory 30 and resets sequential counter (112), and proceeds to acquire the next frame for analysis (101).

In use, the user translates the sensor head 55 over the skin. Linear array 13 can be moved across a section of the breast vertically or horizontally while the user listens to the low pitched humming tone 50. If red LED 40 is illuminated and the alarm tone is triggered during any portion of the scan, the user should scan that area of the breast again (either in the same direction or in another direction, e.g., horizontally). If red LED 40 and the alarm tone are generated again, the user should inspect the area manually and see her physician for further examination.

Other embodiments are within the scope of the following claims.

For example, as an alternative to configuring the tissue examination device 10 as a rectangular array 12 of sensors 14, the tissue examination device can be configured as a linear strip of only one or two rows of sensors 14.

Figure 13:
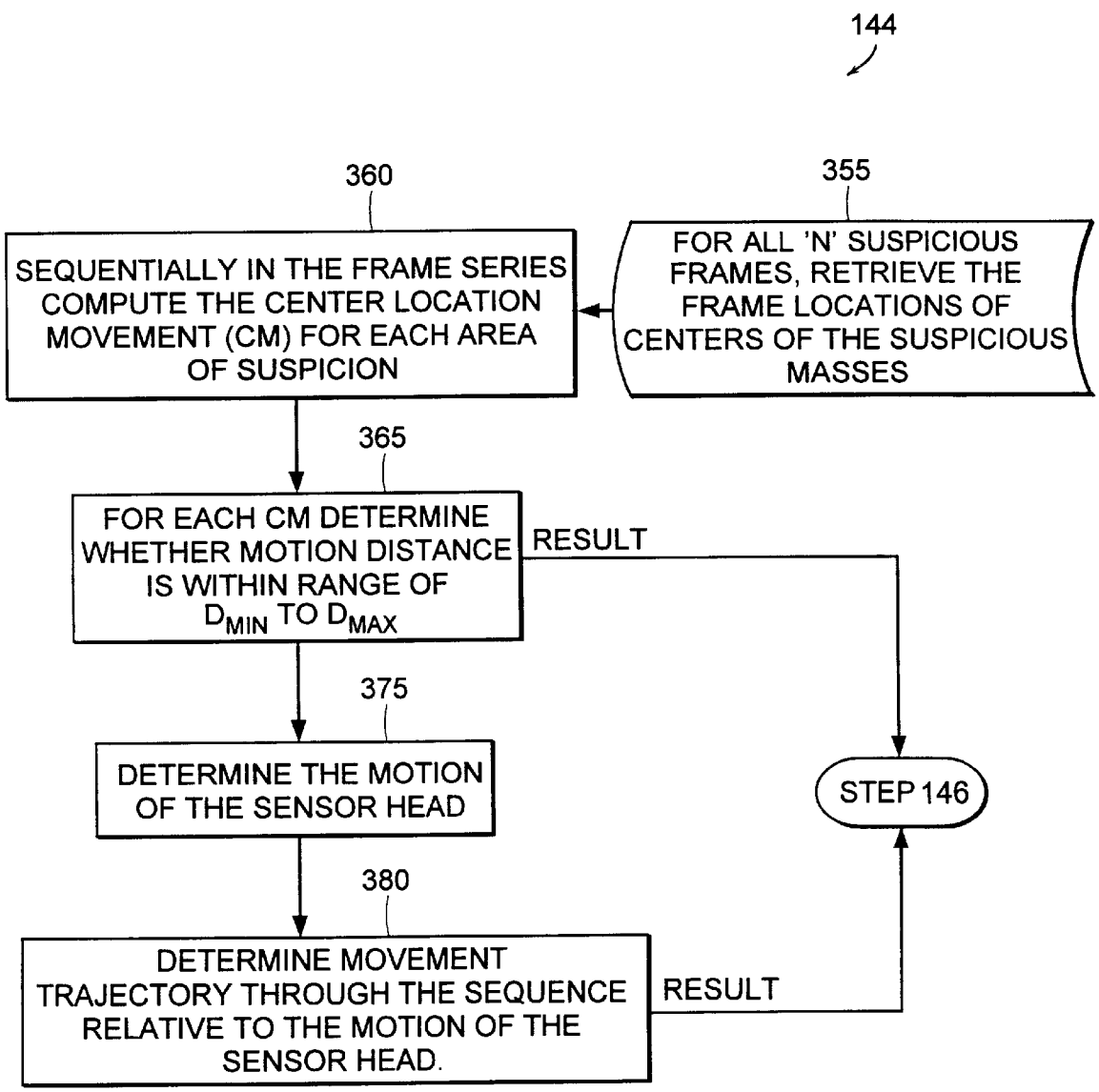
FIG. 13 is a flow chart of a motion test performed during the operation of the tissue examination device of FIG. 1.
Figure 14:
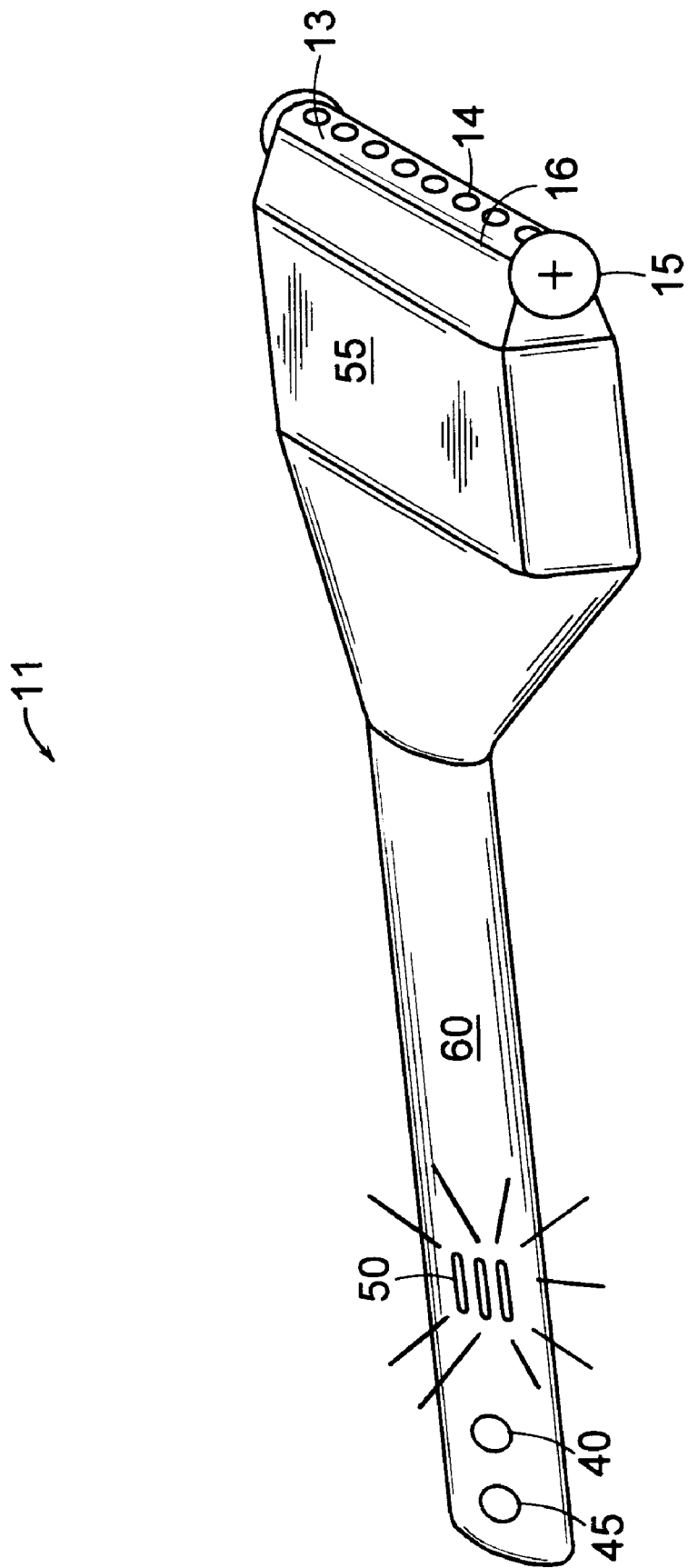
FIG. 14 shows another embodiment of a tissue examination device.

Referring to FIG. 13, tissue examination device 11 includes a linear array 13 of pressure sensors 14 carried on a thin, flexible membrane 16. Linear array 13 is similar to array 12 of device 10, except that the individual pressure sensors 14 are arranged in a single row in a densely packed linear array 13, rather than a orthogonal grid of rows and columns. Pressure sensors 14 generate signals which vary with the pressure applied by contact with the breast tissue. The intensity of the signals will be dependent on the pressure applied by the tissue as the sensor head 55 is pressed against and translated over the tissue.

DSP 24 acquires signals 22 from each pressure sensor 14 and stores the data as a one dimensional array in a row of memory locations 27 in memory 30. DSP 24 constructs a full two-dimensional frame 26a–26n (FIG. 1) by storing successively obtained signals 22 from linear array 13 in successive rows of storage locations 27. Once the sequence of signals 22 are stored to construct a frame, DSP 24 applies the same tests and analyses that were applied for the array sensor 12 (tests that require a comparison between a first and second frame will not be analyzed). These tests enable DSP 24 to differentiate between potential foreign structure and normal tissue, as discussed above.

Device 11 also contains motion sensor (driven by roller 15) that detects motion and enables sensor 14 to permit signals 22 from individual rows to be combined to form the rectangular frame. By being able to form a rectangular array, device 11 allows analysis of a 2-D image. The motion detection capability allows device 11 to analyze movement of the foreign structure when the sensor head 55 translates over the tissue. This is similar to motion test 144.

Other embodiments are within the scope of the following claims.

Other pressure sensor arrays can be used in any of the embodiments discussed herein, and other types of pressure sensors can be used in place of the resistive sensors. Examples include piezoelectric transducers, capacitive sensors, and fiber-optic sensors.

Other techniques for calculating the difference between the highest and lowest amplitudes can alternatively be used.

What is claimed is:

1. A tissue examination device comprising
    a plurality of sensors, arranged in an array, each of said sensors producing a signal in response to pressure imposed on the sensor as the sensors are pressed against the tissue, such pressure varying in accordance with properties of different types of underlying tissue structures, and
    a processor for performing a plurality of processing tests on the signals produced by said sensors and discriminating between the different types of the underlying tissue structures based on results of said tests, said tests comprising
        a first test that includes said processor comparing amplitudes of the signals produced by sensors to a threshold, and evaluating signals that exceed said threshold differently than signals that do not exceed said threshold, and
        a second test in which said processor determines relative locations in said array of sensors that produce signals which exceed said threshold, and a number of said sensors that produce signals that exceed said threshold and which are located adjacent to another one of said sensors in said array that produces a signal which exceeds said threshold.

2. The device of claim 1 wherein said processor determines whether the underlying tissue structure is a normal tissue structure or a potentially foreign tissue structure based on the results of said tests, and further comprising
    circuitry responsive to the determination made by said processor for notifying a user whether the underlying tissue structure is a potentially foreign tissue structure.

3. The device of claim 2 wherein the normal tissue structure includes breast tissue and the potentially foreign tissue structure includes non-breast tissue.

4. The device of claim 3 wherein the normal tissue structure includes a nipple, a rib, or a ligament, and the potentially foreign tissue structure includes a cyst or a solid mass.

5. The device of claim 2 further comprising an indicator actuatable by said circuitry in response to said processor determining that the underlying tissue structure is a potentially foreign tissue structure.

6. The device of claim 5 further comprising a second indicator actuatable by said circuitry in response to said processor determining that the underlying tissue structure is a normal tissue structure.

7. The device of claim 1 wherein said processor generates said threshold based on the amplitudes of said signals.

8. The device of claim 1 wherein said first test further includes said processor determining an average of the amplitudes of said signals that exceed said threshold, and determining whether said average is within a predetermined range of amplitudes.

9. The device of claim 1 wherein said first test further includes said processor determining an average of the amplitudes of said signals that do not exceed said threshold, and determining whether said average exceeds a selected minimum amplitude.

10. The device of claim 9 wherein said processor determines that said first test has passed if said average of the amplitudes of said signals that exceed said threshold is within said predetermined limits and said average of the amplitudes of said signals that do not exceed said threshold exceeds said selected minimum amplitude, and otherwise determines that said first test has failed.

11. A tissue examination device comprising
    a plurality of sensors, arranged in an array, each of said sensors producing a signal in response to pressure imposed on the sensor as the sensors are pressed against the tissue, such pressure varying in accordance with properties of different types of underlying tissue structures, and
    a processor for performing a plurality of processing tests on the signals produced by said sensors and discriminating between the different types of the underlying tissue structures based on results of said tests, said tests comprising a first test that includes said processor comparing amplitudes of the signals produced by said sensors to a threshold, and evaluating signals that exceed said threshold differently than signals that do not exceed said threshold, said processor further being adapted to analyze signals that exceed said threshold to determine whether signals produced by sensors arranged on a periphery of said array are valid.

12. The device of claim 11 wherein said processor performs said analysis by comparing a first number of sensors arranged on the periphery that produce signals which exceed said threshold to a second number of sensors arranged in an interior of said array that produce signals which exceed said threshold, and determining that said signals produced by sensors arranged on the periphery are valid if said second number exceeds said first number by a selected amount.

13. The device of claim 12 wherein said first number of sensors are located adjacent to each other on the periphery, and said second number of sensors are located adjacent to said sensors on the periphery or to each other.

14. The device of claim 12 wherein said processor is further adapted to reduce the amplitudes of said signals produced by said sensors arranged on a periphery of said array below said threshold if said processor determines that said signals are not valid.

15. The device of claim 1 wherein said processor determines that said second test has failed if said number of said sensors does not exceed a selected minimum number.

16. The device of claim 1 wherein said second test further comprises said processor determining whether said number of sensors exceeds by a selected amount an aggregate of said number of sensors and a number of nonadjacent sensors in said array that produce signals that exceed said threshold.

17. The device of claim 16 wherein said processor determines that said second test has passed if said number of sensors exceeds by the selected amount the aggregate of said number of sensors and the number of nonadjacent sensors in said array that produce signals that exceed said threshold, and otherwise determines that said second test has failed.

18. The device of claim 1 wherein said plurality of tests includes a third test in which said processor determines a difference between amplitudes of said signals that exceed said threshold.

19. The device of claim 18 wherein said difference is a ratio between the signal having a highest amplitude and the signal having a lowest amplitude.

20. The device of claim 19 wherein said processor determines that said third test has passed if said ratio exceeds a second threshold, and otherwise determines that said third test has failed.

21. The device of claim 18 further comprising circuitry for successively acquiring a plurality of sets of said signals from said sensors at successively different times as said array is moved over the tissue, each of said sets of signals representing the underlying tissue structures at said times, and a memory for storing said sets of signals, said processor performing said plurality of processing tests on each one of said sets of signals.

22. The device of claim 21 wherein said processor is adapted to perform additional said processing tests on a selected number of said sets of said signals that have passed said first, second, and third tests.

23. The device of claim 22 wherein said processor is adapted to perform said additional processing tests only if said selected number of said sets of said signals are consecutively acquired without interruption by a set of said signals that do not pass either said first, second, or third test.

24. The device of claim 22 wherein said additional tests include a fourth test in which said processor, for each of said sets of said signals:
analyzes the amplitudes of said signals that exceed said threshold to develop for each of the underlying tissue structures a pair of pressure profiles each of which comprises signals produced by sensors in said array that are arranged along a selected dimension of a corresponding underlying tissue structure, a first said pressure profile being oriented along a dimension of maximum flatness of the structure, and a second said pressure profile being oriented along a dimension of minimum flatness of the structure, and
determines an edge profile, a relative stiffness, and a relative curvature of each said underlying tissue structure based on said first and second pressure profiles.

25. The device of claim 24 wherein said processor is adapted to determine said edge profile based on an amount that the amplitude of said signals change from sensor to sensor along said second pressure profile.

26. The device of claim 24 wherein said processor is adapted to determine said relative stiffness based on a difference between the signal having a highest amplitude and the signal having a lowest amplitude in said first pressure profile.

27. The device of claim 24 wherein said processor is adapted to determine said relative curvature based on a flatness of said first pressure profile.

28. The device of claim 24 wherein said processor is adapted to evaluate said edge profile, said relative stiffness, and said relative curvature of each said underlying tissue structure with respect to each other and, based on said evaluation, develop an outcome that indicates a degree of membership of each said underlying tissue structure in a class of foreign tissue structures.

29. The device of claim 28 wherein said processor is adapted to give selective amounts of weights to said edge profile, said relative stiffness, and said relative curvature of each said underlying tissue structure in developing said outcome.

30. The device of claim 24 wherein said additional tests include a fifth test in which said processor evaluates said sets of said signals to determine a manner in which each of the underlying tissue structures move with respect to said array as said array is moved over the tissue.

31. The device of claim 30 wherein said fifth test includes said processor determining
a distance by which each said underlying tissue structure moves with respect to said array, and
a trajectory along which each said underlying tissue structure moves with respect to said array.

32. The device of claim 31 wherein said processor is adapted to evaluate said distance and said trajectory of motion of each said underlying tissue structure with respect to each other and, based on said evaluation, develop an outcome that indicates a degree of membership of each said underlying tissue structure in a class of foreign tissue structures.

33. The device of claim 32 wherein said processor is adapted to give selective amounts of weights to said distance and said trajectory of motion of each said underlying tissue structure in developing said outcome.

34. The device of claim 32 wherein said processor is further adapted to evaluate said edge profile, said relative stiffness, and said relative curvature of each said underlying tissue structure with respect to each other in developing said outcome.

35. The device of claim 34 further comprising circuitry responsive to said outcome developed by said processor for notifying a user whether the underlying tissue structure is a potentially foreign tissue structure.

36. The device of claim 1 further comprising a display for displaying signals that correspond to said amplitudes of said signals generated by said sensors, thereby to enable a user to visualize said distribution.

37. The device of claim 1 wherein said processor is further responsive to said signals generated by said sensors to determine an amount of pressure applied to said plurality of sensors when said sensors are pressed against the body, said processor performing said plurality of processing tests only if the amount of pressure is within a selected range of pressures.

38. The device of claim 37 further comprising circuitry for notifying a user that the amount of pressure is within a selected range of pressures.

39. The device of claim 1 wherein said plurality of sensors are arranged in an array that includes multiple rows of said sensors.

40. The device of claim 1 wherein said plurality of sensors are arranged in an array that includes a single row of said sensors.

41. The device of claim 1 wherein said plurality of sensors include resistive elements.

42. The device of claim 1 wherein said plurality of sensors include piezoelectric elements.

43. The device of claim 1 wherein said plurality of sensors include capacitive sensors.

44. A method of examining tissue, comprising
pressing a plurality of sensors, arranged in an array, against the tissue to cause each of said sensors to produce a signal in response to pressure imposed on the sensor by said pressing, such pressure varying in accordance with properties of different types of underlying tissue structures, and
performing a plurality of processing tests on the signals produced by said sensors and discriminating between the different types of the underlying tissue structures based on results of said tests, said tests comprising
a first test that includes comparing amplitudes of the signals produced by said sensors to a threshold, and evaluating signals that exceed said threshold differently than signals that do not exceed said threshold, and
a second test that includes determining relative locations in said array of sensors that produce signals which exceed said threshold, and a number of said sensors that produce signals that exceed said threshold and which are located adjacent to another one of said sensors in said array that produces a signal which exceeds said threshold.

45. The method of claim 44 further comprising
determining whether the underlying tissue structure is a normal tissue structure or a potentially foreign tissue structure based on the results of said tests, and
responding to said determination by notifying a user whether the underlying tissue structure is a potentially foreign tissue structure.

46. The method of claim 45 wherein the normal tissue structure includes breast tissue and the potentially foreign tissue structure includes non-breast tissue.

47. The method of claim 46 wherein the normal tissue structure includes a nipple, a rib, or a ligament, and the potentially foreign tissue structure includes a cyst or a solid mass.

48. The method of claim 44 further comprising generating said threshold based on the amplitudes of said signals.

49. The method of claim 44 wherein said first test further includes determining an average of the amplitudes of said signals that exceed said threshold, and determining whether said average is within a predetermined range of amplitudes.

50. The method of claim 44 wherein said first test further includes determining an average of the amplitudes of said signals that do not exceed said threshold, and determining whether said average exceeds a selected minimum amplitude.

51. The method of claim 50 further comprising determining that said first test has passed if said average of the amplitudes of said signals that exceed said threshold is within said predetermined limits and said average of the amplitudes of said signals that do not exceed said threshold exceeds said selected minimum amplitude, and otherwise determining that said first test has failed.

52. A method of examining tissue comprising
pressing a plurality of sensors, arranged in an array, against the tissue to cause each of said sensors to produce a signal in response to pressure imposed on the sensor by said pressing, such pressure varying in accordance with properties of different types of underlying tissue structures, and
performing a plurality of processing tests on the signals produced by said sensors and discriminating between the different types of the underlying tissue structures based on results of said tests, said tests comprising a first test that includes comparing amplitudes of the signals produced by said sensors to a threshold, and evaluating signals that exceed said threshold differently than signals that do not exceed said threshold, and
analyzing signals that exceed said threshold to determine whether signals produced by sensors arranged on a periphery of said array are valid.

53. The method of claim 52 further comprising performing said analysis by comparing a first number of sensors arranged on the periphery that produce signals which exceed said threshold to a second number of sensors arranged in an interior of said array that produce signals which exceed said threshold, and determining that said signals produced by sensors arranged on the periphery are valid if said second number exceeds said first number by a selected amount.

54. The method of claim 53 wherein said first number of sensors are located adjacent to each other on the periphery, and said second number of sensors are located adjacent to said sensors on the periphery or to each other.

55. The method of claim 53 further comprising reducing the amplitudes of said signals produced by said sensors arranged on a periphery of said array below said threshold if said signals are determined to be not valid.

56. The method of claim 44 further comprising determining that said second test has failed if said number of said sensors does not exceed a selected minimum number.

57. The method of claim 44 wherein said second test further comprises determining whether said number of sensors exceeds by a selected amount an aggregate of said number of sensors and a number of nonadjacent sensors in said array that produce signals that exceed said threshold.

58. The method of claim 57 further comprising determining that said second test has passed if said number of sensors exceeds by the selected amount the aggregate of said number of sensors and the number of nonadjacent sensors in said array that produce signals that exceed said threshold, and otherwise determining that said second test has failed.

59. The method of claim 46 wherein said plurality of tests includes a third test comprising determining a difference between amplitudes of said signals that exceed said threshold.

60. The method of claim 59 wherein said difference is a ratio between the signal having a highest amplitude and the signal having a lowest amplitude.

61. The method of claim 60 further comprising determining that said third test has passed if said ratio exceeds a second threshold, and otherwise determines that said third test has failed.

62. The method of claim 59 further comprising successively acquiring a plurality of sets of said signals from said sensors at successively different times as said array is moved over the tissue, each of said sets of signals representing the underlying tissue structures at said times, storing said sets of signals, and performing said plurality of processing tests on each one of said sets of signals.

63. The method of claim 62 further comprising performing additional said processing tests on a selected number of said sets of said signals that have passed said first, second, and third tests.

64. The method of claim 63 further comprising performing said additional processing tests only if said selected number of said sets of said signals are consecutively acquired without interruption by a set of said signals that do not pass either said first, second, or third test.

65. The method of claim 62 wherein said additional tests include a fourth test that comprises, for each of said sets of said signals:

analyzing the amplitudes of said signals that exceed said threshold to develop for each of the underlying tissue structures a pair of pressure profiles each of which comprises signals produced by sensors in said array that are arranged along a selected dimension of a corresponding underlying tissue structure, a first said pressure profile being oriented along a dimension of maximum flatness of the structure, and a second said pressure profile being oriented along a dimension of minimum flatness of the structure, and determining an edge profile, a relative stiffness, and a relative curvature of each said underlying tissue structure based on said first and second pressure profiles.

66. The method of claim 65 further comprising determining said edge profile based on an amount that the amplitude of said signals change from sensor to sensor along said second pressure profile.

67. The method of claim 65 further comprising determining said relative stiffness based on a difference between the signal having a highest amplitude and the signal having a lowest amplitude in said first pressure profile.

68. The method of claim 65 further comprising determining said relative curvature based on a flatness of said first pressure profile.

69. The method of claim 65 further comprising evaluating said edge profile, said relative stiffness, and said relative curvature of each said underlying tissue structure with respect to each other and, based on said evaluation, developing an outcome that indicates a degree of membership of each said underlying tissue structure in a class of foreign tissue structures.

70. The method of claim 69 further comprising giving selective amounts of weights to said edge profile, said relative stiffness, and said relative curvature of each said underlying tissue structure in developing said outcome.

71. The method of claim 65 wherein said additional tests include a fifth test comprising evaluating said sets of said signals to determine a manner in which each of the underlying tissue structures moves with respect to said array as said array is moved over the tissue.

72. The method of claim 71 wherein said fifth test includes determining a distance by which each said underlying tissue structure moves with respect to said array, and a trajectory along which each said underlying tissue structure moves with respect to said array.

73. The method of claim 72 further comprising evaluating said distance and said trajectory of motion of each said underlying tissue structure with respect to each other and, based on said evaluation, developing an outcome that indicates a degree of membership of each said underlying tissue structure in a class of foreign tissue structures.

74. The method of claim 73 further comprising giving selective amounts of weights to said distance and said trajectory of motion of each said underlying tissue structure in developing said outcome.

75. The method of claim 73 further comprising evaluating said edge profile, said relative stiffness, and said relative curvature of each said underlying tissue structure with respect to each other in developing said outcome.

76. The method of claim 75 further comprising responding to said developed outcome by notifying a user whether the underlying tissue structure is a potentially foreign tissue structure.

77. The method of claim 44 further comprising displaying signals that correspond to said amplitudes of said signals generated by said sensors, thereby to enable a user to visualize said distribution.

78. The method of claim 44 further comprising responding to said signals produced by said sensors by determining an amount of pressure applied to said plurality of sensors when said sensors are pressed against the body, and performing said plurality of processing tests only if the amount of pressure is within a selected range of pressures.

79. The method of claim 78 further notifying a user that the amount of pressure is within a selected range of pressures.

80. The method of claim 44 further comprising arranging said plurality of sensors in an array that includes multiple rows of said sensors.

81. The method of claim 44 further comprising arranging said plurality of sensors in an array that includes a single row of said sensors.

82. A tissue examination device comprising a plurality of sensors each of which produces a signal in response to pressure imposed on the sensor as the sensors are pressed against the tissue, the signals representing pressure signatures associated with different types of underlying tissue structures, and a processor for processing the signals to determine a plurality of characteristics of the pressure signatures and discriminating between the different types of the underlying tissue structures based on the determined characteristics, the plurality of characteristics including shapes of the pressure signatures.

83. The device of claim 82 wherein the shapes are characterized by at least one of edge profile, relative stiffness, and relative curvature of the pressure signatures.

84. A tissue examination device comprising a plurality of sensors each of which produces a signal in response to pressure imposed on the sensor as the sensors are pressed against the tissue, the signals representing pressure signatures associated with different types of underlying tissue structures, and a processor for processing the signals to determine a plurality of characteristics of the pressure signatures and discriminating between the different types of the underlying tissue structures based on the determined characteristics, the plurality of characteristics including a manner in which the pressure signatures change as the sensors are moved over the tissue.

85. A tissue examination device comprising a plurality of sensors each of which produces a signal in response to pressure imposed on the sensor as the sensors are pressed against the tissue, the signals representing pressure signatures associated with different types of underlying tissue structures, and a processor for processing the signals to determine a plurality of characteristics of the pressure signatures and discriminating between the different types of the underlying tissue structures based on the determined characteristics, the plurality of characteristics including continuity of the signals having an amplitude greater than a selected threshold in the pressure signatures.

86. A tissue examination device comprising a plurality of sensors each of which produces a signal in response to pressure imposed on the sensor as the sensors are pressed against the tissue, the signals representing pressure signatures associated with different types of underlying tissue structures, and a processor for processing the signals to determine a plurality of characteristics of the pressure signatures and discriminating between the different types of the underlying tissue structures based on the determined characteristics, the plurality of characteristics including size of the pressure signatures.

87. A tissue examination device comprising a plurality of sensors each of which produces a signal in response to pressure imposed on the sensor as the sensors are pressed against the tissue, the signals representing pressure signatures associated with different types of underlying tissue structures, and a processor for processing the signals to determine a plurality of characteristics of the pressure signatures and discriminating between the different types of the underlying tissue structures based on the determined characteristics, the plurality of characteristics including peakness or flatness of the pressure signatures.

88. A method of examining tissue comprising pressing a plurality of sensors against the tissue to cause each of the sensors to produce a signal in response to the pressure imposed on the sensor by said pressing, the signals representing pressure signatures associated with different types of underlying tissue structures, and processing the signals to determine characteristics of the pressure signatures and discriminating between the different types of the underlying tissue structures based on the determined characteristics, the plurality of characteristics including shapes of the pressure signatures.

89. The method of claim 88 wherein the shapes are characterized by at least one of edge profile, relative stiffness, and relative curvature of the pressure signatures.

90. A method of examining tissue comprising pressing a plurality of sensors against the tissue to cause each of the sensors to produce a signal in response to the pressure imposed on the sensor by said pressing, the signals representing pressure signatures associated with different types of underlying tissue structures, and processing the signals to determine characteristics of the pressure signatures and discriminating between the different types of the underlying tissue structures based on the determined characteristics, the plurality of characteristics including a manner in which the pressure signatures change as the sensors are moved over the tissue.

91. A method of examining tissue comprising pressing a plurality of sensors against the tissue to cause each of the sensors to produce a signal in response to the pressure imposed on the sensor by said pressing, the signals representing pressure signatures associated with different types of underlying tissue structures, and processing the signals to determine characteristics of the pressure signatures and discriminating between the different types of the underlying tissue structures based on the determined characteristics, the plurality of characteristics including continuity of the signals having an amplitude greater than a selected threshold in the pressure signatures.

92. A method of examining tissue comprising pressing a plurality of sensors against the tissue to cause each of the sensors to produce a signal in response to the pressure imposed on the sensor by said pressing, the signals representing pressure signatures associated with different types of underlying tissue structures, and processing the signals to determine characteristics of the pressure signatures and discriminating between the different types of the underlying tissue structures based on the determined characteristics, the plurality of characteristics including size of the pressure signatures.

93. A method of examining tissue comprising pressing a plurality of sensors against the tissue to cause each of the sensors to produce a signal in response to the pressure imposed on the sensor by said pressing, the signals representing pressure signatures associated with different types of underlying tissue structures, and processing the signals to determine characteristics of the pressure signatures and discriminating between the different types of the underlying tissue structures based on the determined characteristics, the plurality of characteristics including peakness or flatness of the pressure signatures.

* * * * *

UNITED STATES PATENT AND TRADEMARK OFFICE
CERTIFICATE OF CORRECTION

PATENT NO. : 5,989,199
DATED : NOVEMBER 23, 1999
INVENTOR(S) : MICHAEL A. CUNDARI ET AL.

It is certified that error appears in the above-identified patent and that said Letters Patent is hereby corrected as shown below:

Col. 8, line 45, replace "whet-her" with --whether--.

Col. 8, line 66, after "profile.)" start a new paragraph.

Col. 16, line 8, replace "$P_{L\text{-}PS}$" with --$P_L\text{-}P_S$--.

Col. 22, claim 59, line 61, replace "46" with --48--.

Col. 23, claim 65, line 23, replace "62" with --63--.

Signed and Sealed this

Twenty-sixth Day of December, 2000

Attest:

Q. TODD DICKINSON

*Attesting Officer*   *Director of Patents and Trademarks*